United States Patent
Yuan

(10) Patent No.: US 10,267,786 B2
(45) Date of Patent: Apr. 23, 2019

(54) SYSTEMS AND METHODS FOR HIGH-RESOLUTION IMAGING

(71) Applicant: Board of Regents, The University of Texas System, Austin, TX (US)

(72) Inventor: Baohong Yuan, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 729 days.

(21) Appl. No.: 14/162,375

(22) Filed: Jan. 23, 2014

(65) Prior Publication Data

US 2014/0206031 A1  Jul. 24, 2014

Related U.S. Application Data

(60) Provisional application No. 61/756,065, filed on Jan. 24, 2013.

(51) Int. Cl.
| | |
|---|---|
| *G01N 33/00* | (2006.01) |
| *G01N 33/50* | (2006.01) |
| *G01N 33/542* | (2006.01) |
| *A61K 41/00* | (2006.01) |
| *A61K 49/00* | (2006.01) |

(52) U.S. Cl.
CPC ..... *G01N 33/5091* (2013.01); *A61K 41/0028* (2013.01); *A61K 49/0034* (2013.01); *G01N 33/542* (2013.01)

(58) Field of Classification Search
CPC combination set(s) only.
See application file for complete search history.

(56) References Cited

U.S. PATENT DOCUMENTS

| | | | |
|---|---|---|---|
| 2006/0036069 A1* | 2/2006 | Kooi | G01K 11/12 528/499 |
| 2006/0184049 A1 | 8/2006 | Tsujita | |
| 2009/0178483 A1* | 7/2009 | Angelsen | A61B 8/08 73/597 |

(Continued)

OTHER PUBLICATIONS

Wang et al., "Biomedical Optics: principles and Imaging", Wiley Publications, 2007, p. 13.*

(Continued)

*Primary Examiner* — Joseph M Santos Rodriguez
(74) *Attorney, Agent, or Firm* — John P. Zimmer; Nexsen Pruet, PLLC

(57) ABSTRACT

In one aspect, methods of imaging are described herein. In some embodiments, a method of imaging described herein comprises disposing a population of ultrasound-switchable fluorophores in a biological environment, the fluorophores having a switching threshold between an off state and an on state; exposing the biological environment to an ultrasound beam to create an activation region within the biological environment; switching at least one of the fluorophores within the activation region from the off state to the on state; exciting the at least one fluorophore with a beam of electromagnetic radiation; and detecting light emitted by the fluorophore. In some embodiments, the activation region has a maximum negative pressure and/or maximum temperature and the switching threshold of the at least one fluorophore is at least about 50 percent of the maximum negative pressure or at least about 50 percent of the maximum temperature of the activation region.

19 Claims, 12 Drawing Sheets

(56) References Cited

U.S. PATENT DOCUMENTS

2013/0030289 A1 1/2013 Zhu et al.
2013/0189188 A1 7/2013 Gulsen et al.

OTHER PUBLICATIONS

Alper Corlu et al., "Three-Dimensional in vivo fluorescence diffuse optical tomography of breast cancer in humans", Optics Express, vol. 15, No. 11, May 28, 2007, pp. 6696-6716.

Lihong V. Wang et al., "Photoacoustic Tomography: In Vivo Imaging from Organelles to Organs", Science Magazine, vol. 335, Mar. 23, 2012, pp. 1458-1462.

Steffen G. Resink et al., "State-of-the-art of acousto-optic sensing and imaging of turbid media", Journal of Biomedical Optics, vol. 17(4), 040901, Apr. 2012, pp. 040901-1-040901-10.

Yuting Lin et al., "Temperature-modulated fluorescence tomography in a turbid media", AIP Applied Physics Letters 100, 073702 (2012), pp. 073702-1-073702-4.

Yuting Lin et al., "Temperature-modulated fluorescence tomography based on both concentration and lifetime contrast", Journal of Biomedical Optics, vol. 17(5), 056007 May 2012, pp. 056007-1-056007-4.

Baohong Yuan et al., "High-resolution imaging in a deep turbid medium based on an ultrasound-switchable fluorescence technique", Applied Physics Letters 101, 033703, 2012, pp. 033703-1-033703-5.

Baohong Yuan et al., "Ultrasound-modulated fluorescence based on a fluorophore-quencher-labeled microbubble system", Journal of Biomedical Optics, vol. 14(2), 024043, Mar./Apr. 2009, pp. 024034-1-024034-11.

E. A. Filonenko et al., "Effect of Acoustic Nonlinearity on Heating of Biological Tissue by High-Intensity Focused Ultrasound", Acoustical Physics, vol. 47, No. 4, 2001, pp. 468-475.

Joshua E. Soneson, "A User-Friendly Software Package for HIFU Simulation", Center for Devices and Radiological Health, US Food and Drug Administration, Silver Spring, Maryland, 20993, 5 pages.

Baohong Yuan et al., "Microbubble-enhanced ultrasound-modulated fluorescence in a turbid medium", AIP Applied Physics Letters 95, 181113 (2009), pp. 181113-1-18113-3.

F. Stuart Foster et al., "Advances in Ultrasound Biomicroscopy", Ultrasound in Med. & Biol., vol. 26, No. 1, 2000, pp. 1-27.

John W. Hunt et al., "Ultrasound Transducers for Pulse-Echo Medical Imaging", IEEE Transactions on Biomedical Engineering, vol. BME-30, No. 8, Aug. 1983, pp. 453-481.

Pei, Y et al., "High Resolution imaging beyond the acoustic diffraction limit in deep tissue via ultrasound-switchable NIR fluorescence", Scientific Reports 4, Article 4690, Apr. 15, 2014 [retrieved on Apr. 12, 2016] from the Internet <URL; http://www.nature.com/articles/srep04690>; entire document.

\* cited by examiner

P(TBAm-NIPAM)

P(NIPAM-AAm)

PNIPAM

ICG

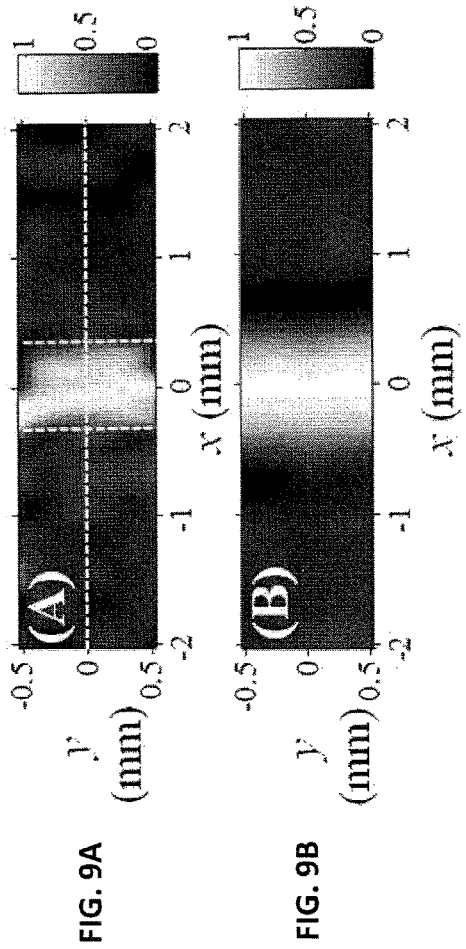
FIG. 9A
FIG. 9B
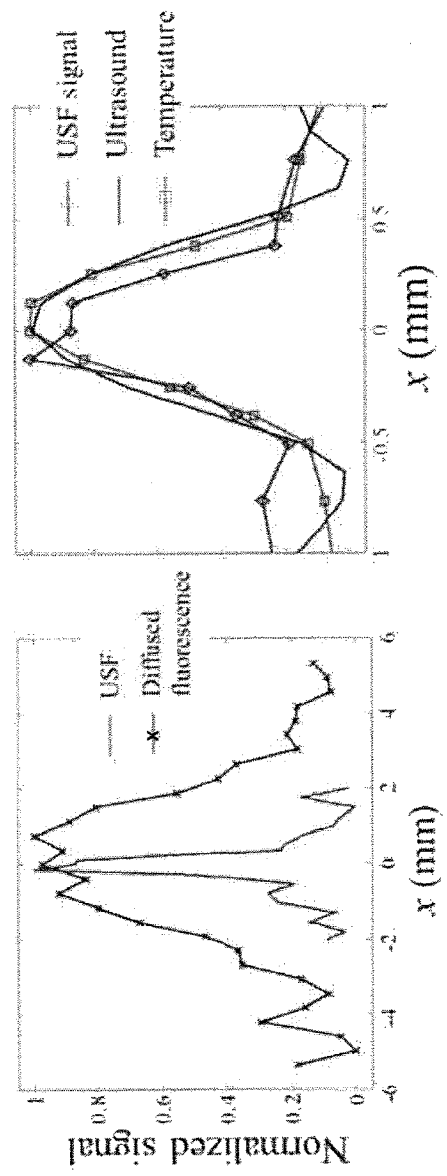
FIG. 9C
FIG. 9D

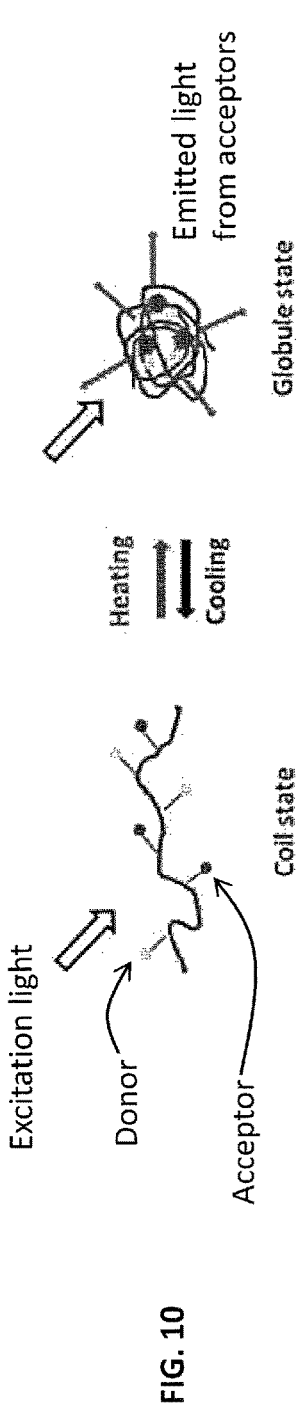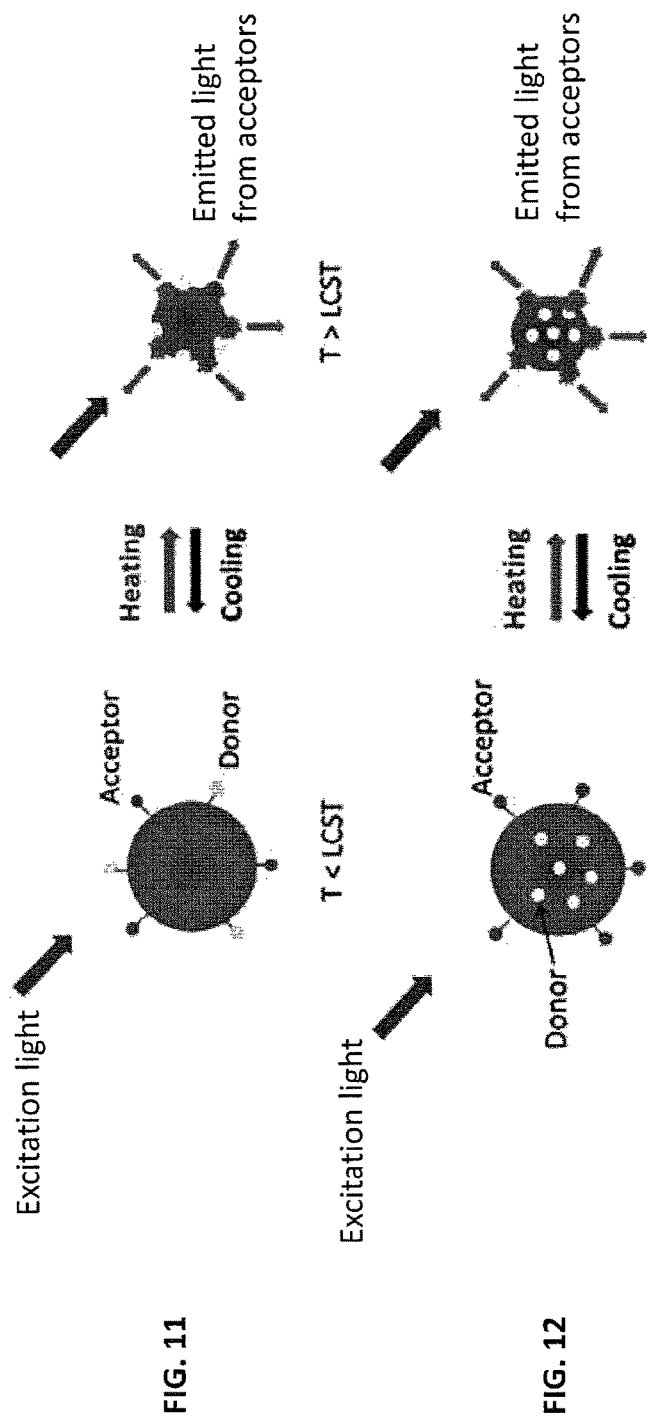
FIG. 10
FIG. 11
FIG. 12

ADPDI Cyanocinnamic acid

SYSTEMS AND METHODS FOR HIGH-RESOLUTION IMAGING

CROSS REFERENCE TO RELATED APPLICATION

This application claims priority pursuant to 35 U.S.C. § 119(e) to U.S. Provisional Patent Application Ser. No. 61/756,065, filed on Jan. 24, 2013, which is hereby incorporated by reference in its entirety.

STATEMENT REGARDING FEDERALLY SPONSORED RESEARCH

This invention was made with government support under contract 7R15EB012312-02 awarded by the National Institutes of Health through the National Institute of Biomedical Imaging and Bioengineering, contract RP120052 awarded by the Cancer Prevention and Research Institute of Texas, and contract CBET-1253199 awarded by the National Science Foundation. The government has certain rights in the invention.

FIELD

This invention relates to systems and methods for high-resolution imaging and, in particular, to imaging using ultrasound-switchable fluorescence (USF).

BACKGROUND

Fluorescence imaging in deep biological tissue can provide important information regarding tissue structure, function, and dysfunction. However, some previous fluorescence imaging techniques are limited in penetration depth and/or spatial resolution due to strong light scattering in deep tissue. As a result, such methods can have reduced effectiveness for many tissue biology and/or clinical applications.

Therefore, there exists a need for improved systems and methods for high-resolution imaging, particularly for imaging deep biological tissue.

SUMMARY

In one aspect, methods of imaging are described herein which, in some cases, can provide one or more advantages compared to other methods. For example, in some embodiments, a method described herein can provide imaging of deep biological tissue with a resolution beyond the acoustic diffraction limit and can further exhibit an improved imaging depth-to-imaging-resolution ratio (DRR). In addition, a fluorophore of a method described herein, in some cases, can exhibit a large on/off ratio of fluorescence intensity or lifetime and/or a narrow transition bandwidth between on and off states. Further, a fluorophore of a method described herein can also exhibit a tunable threshold between on and off states.

A method described herein, in some embodiments, comprises disposing a population of ultrasound-switchable fluorophores in a biological environment, the fluorophores having a switching threshold between an off state and an on state, and exposing the biological environment to an ultrasound beam to create an activation region within the biological environment. The method further comprises switching at least one of the fluorophores within the activation region from the off state to the on state, exciting the at least one fluorophore with a beam of electromagnetic radiation, and detecting light emitted by the at least one fluorophore. In some embodiments, the activation region has a maximum negative pressure and/or a maximum temperature, and the switching threshold of the at least one fluorophore is at least about 50 percent of the maximum negative pressure of the activation region or at least about 50 percent of the maximum temperature of the activation region. In some cases, for instance, the fluorophores have a switching temperature threshold between an off state and an on state, and the activation region has a maximum temperature that is greater than or equal to the switching temperature threshold of the fluorophores.

In addition, in some embodiments, a method described herein comprises exposing the biological environment to a plurality of ultrasound beams from a plurality of different directions, wherein the focal zones of the ultrasound beams at least partially overlap. Further, in some such cases, the switching threshold of the fluorophores is greater than the maximum temperature or maximum negative pressure provided by the focal zone of one of the ultrasound beams alone.

Moreover, in some cases, a method described herein further comprises exposing the biological environment to a pulsed beam of electromagnetic radiation prior to exposing the biological environment to the ultrasound beam, the pulsed beam having a pulse duration of no greater than 100 picoseconds (ps), wherein the pulse duration is defined as the full width at half maximum of the optical power of the pulse over time.

In some embodiments, an ultrasound-switchable fluorophore used in a method described herein comprises a Förster resonance energy transfer (FRET) donor species and a FRET acceptor species. In some such instances, the distance between the FRET donor species and the FRET acceptor species of the fluorophore is altered by the presence of an ultrasound beam. For example, in some embodiments, a fluorophore comprises a microbubble comprising one or more FRET donor species and one or more FRET acceptor species attached to the surface of the microbubble. In other cases, an ultrasound-switchable fluorophore used in a method described herein comprises a thermoresponsive polymer. Additionally, in some cases, a thermoresponsive polymer of a fluorophore described herein comprises one or more fluorescent moieties or is conjugated to one or more fluorescent species, such as one or more fluorescent dye molecules. In other instances, a fluorophore described herein comprises a fluorescent material dispersed in and/or attached to the surface of a thermoresponsive polymer nanoparticle. Moreover, in some embodiments, an ultrasound-switchable fluorophore described herein exhibits a fluorescence emission profile in the near infrared (NIR), an on-to-off ratio in fluorescence intensity ($I_{On}/I_{Off}$) of at least about 2, an on-to-off ratio in fluorescence lifetime ($\tau_{On}/\tau_{Off}$) of at least about 1.5, and/or a transition bandwidth between on and off states ($T_{BW}$) of no greater than about 10° C.

In addition, in some embodiments, the biological environment of a method described herein comprises deep tissue. In some cases, the biological environment comprises tumor vasculature. Moreover, in some instances, a method described herein exhibits a penetration depth/resolution ratio of at least about 100.

These and other embodiments are described in more detail in the detailed description which follows.

BRIEF DESCRIPTION OF THE FIGURES

FIG. 9A illustrates a USF image obtained by a method according to one embodiment described herein.

FIG. 9B illustrates a comparative image corresponding to the image of FIG. 9A.

FIG. 9C illustrates a fluorescence profile obtained by a method according to one embodiment described herein.

FIG. 9D illustrates a fluorescence profile obtained by a method according to one embodiment described herein.

FIG. 10 illustrates an ultrasound-switchable fluorescence process according to one embodiment of a method described herein.

FIG. 11 illustrates an ultrasound-switchable fluorescence process according to one embodiment of a method described herein.

FIG. 12 illustrates an ultrasound-switchable fluorescence process according to one embodiment of a method described herein.

DETAILED DESCRIPTION

Figure 1:
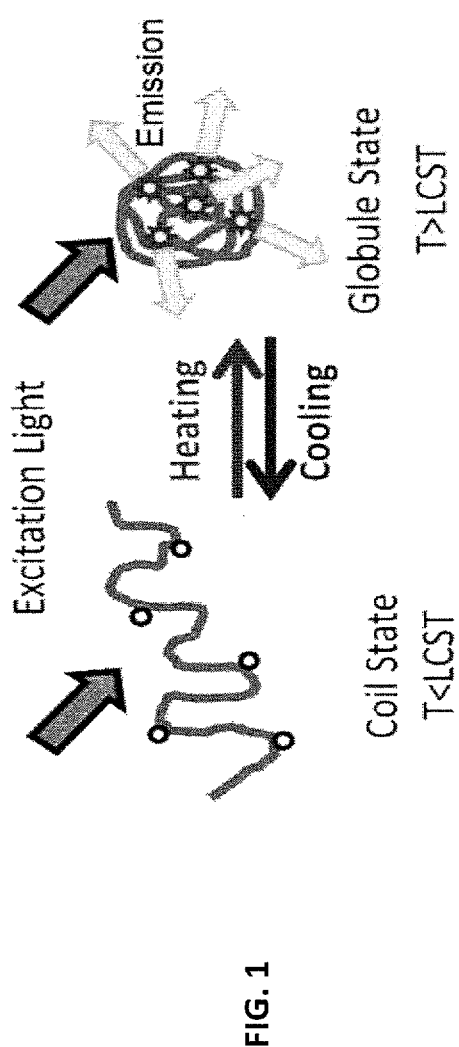
FIG. 1 illustrates an ultrasound-switchable fluorescence process according to one embodiment of a method described herein.

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

In one aspect, methods of imaging are described herein. In some embodiments, a method of imaging comprises disposing a population of ultrasound-switchable fluorophores in a biological environment, the fluorophores having a switching threshold between an off state and an on state; and exposing the biological environment to an ultrasound beam to create an activation region within the biological environment, the activation region having a maximum negative pressure and a maximum temperature, wherein the switching threshold of the at least one fluorophore is at least about 50 percent of the maximum negative pressure or at least about 50 percent of the maximum temperature of the activation region. The method further comprises switching at least one of the fluorophores within the activation region from the off state to the on state; exciting the at least one fluorophore with a beam of electromagnetic radiation; and detecting light emitted by the at least one fluorophore. In some embodiments, the switching threshold of the at least one fluorophore is at least about 60 percent or at least about 70 percent of the maximum negative pressure or maximum temperature of the activation region. In some cases, the switching threshold of the at least one fluorophore is between about 60 percent and about 100 percent, between about 60 percent and about 90 percent, between about 70 percent and about 100 percent, between about 70 percent and about 95 percent, or between about 70 percent and about 90 percent of the maximum negative pressure or maximum temperature of the activation region. As described further hereinbelow, selecting such a switching threshold, in some cases, can permit improved imaging resolution by effectively reducing the volume of the activation region to a size below the size of the focal zone of the ultrasonic beam used to form the activation region.

In other embodiments, a method of imaging comprises disposing a population of ultrasound-switchable fluorophores in a biological environment, the fluorophores having a switching threshold between an off state and an on state; and exposing the biological environment to a plurality of ultrasound beams from a plurality of different directions to create an activation region within the biological environment, the focal zones of the ultrasound beams at least partially overlapping. In some cases, for example, two orthogonal ultrasound beams are used. Additionally, in some instances, the switching threshold of the fluorophores is greater than the maximum negative pressure or the maximum temperature provided by the focal zone of one of the ultrasound beams alone. The method further comprises switching at least one of the fluorophores within the activation region from the off state to the on state; exciting the at least one fluorophore with a beam of electromagnetic radiation; and detecting light emitted by the at least one fluorophore. As described further hereinbelow, the use of multiple ultrasound beams in a manner described herein can permit improved imaging resolution by reducing the size of the activation region.

In still other embodiments, a method of imaging comprises disposing a population of ultrasound-switchable fluorophores in a biological environment, the fluorophores having a switching threshold between an off state and an on state; and exposing the biological environment to a pulsed beam of electromagnetic radiation, the pulsed beam having a pulse duration of no greater than 100 ps, based on the FWHM of the optical power of the pulsed beam over time. The method further comprises exposing the biological environment to an ultrasound beam to create an activation region within the biological environment; switching at least one of the fluorophores within the activation region from the off state to the on state; exciting the at least one fluorophore with a second beam of electromagnetic radiation; and detecting light emitted by the at least one fluorophore. Moreover, in some cases, the pulsed beam has a pulse duration of no greater than about 50 ps or no greater than about 10 ps. In some embodiments, the pulsed beam has a pulse duration between about 1 ps and about 100 ps, between about 1 ps and about 10 ps, between about 1 ps and about 50 ps, between about 10 ps and about 100 ps, or between about 10 ps and about 50 ps. As described further hereinbelow, exposing the biological environment to a pulsed beam of electromagnetic radiation in a manner described herein, in some embodiments, can improve the signal-to-noise ratio (SNR) of the method by permitting temporal separation of the detection of the fluorophore emission, compared to the emission from other species present in the biological environment. Thus, in some cases, the step of detecting light emitted by the at least one fluorophore is carried out after a delay corresponding to the fluorescence lifetime of such other species. In addition, in some embodiments, the wavelength of the pulsed beam is selected to substantially overlap with the absorption profile of one or more species present in the biological environment.

Turning now to specific steps of methods, methods of imaging described herein comprise disposing a population of ultrasound-switchable fluorophores in a biological environment. Any biological environment not inconsistent with the objectives of the present invention may be used. In some cases, for example, the biological environment is an in vivo environment, such as a tissue, organ, blood vessel, or other portion of a living organism. In some embodiments, the biological environment comprises a tumor or tumor vasculature. In other cases, a biological environment comprises an in vitro environment, such as a tissue culture. The biological environment of a method described herein can also comprise or be replaced by a biological phantom material or tissue-mimicking phantom material, such as an agar, silicone, polyvinyl alcohol (PVA) gel, polyacrylamide (PAA) gel, or a dispersion of an oil in gelatin. Other phantom materials may also be used.

Moreover, in some embodiments, a biological environment comprises deep tissue. "Deep" tissue, for reference purposes herein, comprises tissue (or, in the case of a phantom material, an interior region of the phantom material) that is located at least about 1 cm below the outer surface of the organism, tissue culture, or other larger structure associated with the biological environment (such as, in the case of a phantom material, the outer surface of the phantom material). In some embodiments, for instance, deep tissue is located between about 1 cm and about 10 cm or between about 1 cm and about 5 cm below an outer surface. In some cases, deep tissue is located more than 10 cm below an outer surface. Further, an outer surface, in some embodiments, comprises the surface of the skin of an organism.

In addition, any ultrasound-switchable fluorophore not inconsistent with the objectives of the present invention may be used. An "ultrasound-switchable" fluorophore, for reference purposes herein, comprises a fluorophore operable to switch between an on state and an off state in response to exposure to an ultrasound beam. The ultrasound beam can be either directly or indirectly responsible for the switching response of the fluorophore. For example, in some cases, the ultrasound beam interacts directly with the fluorophore, resulting in a switch between fluorescence states of the fluorophore. In other cases, the ultrasound beam interacts directly with the immediate environment or microenvironment of the fluorophore and changes at least one property of the fluorophore's microenvironment. In such cases, the fluorophore can switch between on and off fluorescence states in response to the environmental change induced by the ultrasound beam. Thus, the fluorophore can be indirectly switchable in response to exposure to an ultrasound beam.

The "on" state of a fluorophore, for reference purposes herein, comprises either (1) a state at which the fluorescence intensity of the fluorophore is relatively high compared to the "off" state of the fluorophore, at which the fluorescence intensity is relatively low; or (2) a state at which the fluorescence lifetime of the fluorophore is relatively long compared to the "off" state of the fluorophore, at which the fluorescence lifetime is relatively short. Further, in both cases, the on and off states substantially define a step function in the fluorescence intensity or lifetime profile when plotted as a function of a critical switching parameter such as temperature or negative pressure. A fluorophore having a longer lifetime in an on state than an off state can be particularly suitable for use in methods described herein using time-gated or time-delayed detection of emitted photons from fluorophores, such as time-gated detection in which only those photons received after a relatively long delay following excitation are counted by the detector as part of the USF signal. In some cases, the on state of a fluorophore exhibits at least about 70 percent, at least about 80 percent, or at least about 90 percent of the theoretical maximum fluorescence intensity of the fluorophore, and the off state of the fluorophore exhibits no more than about 50 percent, no more than about 30 percent, no more than about 10 percent, or no more than about 5 percent of the theoretical maximum fluorescence intensity of the fluorophore.

The physical cause for the existence of an on state versus an off state can vary. For example, in some cases, the fluorescence intensity or fluorescence lifetime of a fluorophore changes dues to a conformational or chemical change of the fluorophore in response to a change in environmental conditions, such as exhibited by some thermoresponsive polymers, pH-sensitive chemical species, or pressure sensitive materials. In some cases, the fluorescence intensity or fluorescence lifetime of a fluorophore changes in response to internal fluorescence quenching, wherein such quenching can be directly or indirectly induced by the presence of ultrasound.

For example, in some embodiments, a fluorophore described herein comprises a FRET donor species and a FRET acceptor species, and the distance between the FRET donor species and the FRET acceptor species is altered by the presence of an ultrasound beam. The FRET donor species can be a first fluorescent species or other chromophore, and the FRET acceptor species can be a second fluorescent species or other chromophore. In such cases, as understood by one of ordinary skill in the art, FRET energy transfer between the donor species and the acceptor species can result in quenching of the fluorescence of the donor species. Thus, the acceptor species can be considered to be a fluorescence quenching species of the fluorophore. Any donor-acceptor pair not inconsistent with the objectives of the present invention may be used in FRET-based fluorophores described herein. For example, in some cases, the donor species comprises Alexa Fluor 546 and the acceptor species comprise Alexa Fluor 647. Other combinations of acceptor species and donor species are also possible.

In some embodiments, a fluorophore described herein comprises a microbubble comprising one or more FRET donor species and one or more FRET acceptor species attached to the exterior surface of the microbubble, wherein the microbubble is operable to change in size in response to the presence of an ultrasound beam. The change in size can increase or decrease the distance between the FRET donor species and the FRET acceptor species, thus reducing or increasing the FRET energy transfer efficiency. As a result, the fluorescence quenching and the overall fluorescence intensity of the microbubble can vary based on the size of the microbubble.

A microbubble described herein can have any size and be formed of any chemical species not inconsistent with the objectives of the present invention. In some cases, a microbubble has a diameter between about 1 µm and about 10 µm or between about 1 µm and about 5 µm. Other sizes of microbubbles may also be used. Moreover, in some embodiments, a microbubble described herein comprises a gas core surrounded by a shell formed from a polymeric material, such an organic polymeric material. In other cases, the shell is formed from a lipid material. In some embodiments, a microbubble comprises a shell formed from one or more of albumin, galactose, lipid, and sulfur hexafluoride. In addition, the gas core of a microbubble described herein can comprise one or more of air, nitrogen, and a perfluorocarbon such as octafluoropropane. Moreover, in some cases, a microbubble described herein is formed from a commercially available microbubble, such as a SonoVue™, Optison™, Imagent™, Definity™, or Targestar™ microbubble. A FRET donor and/or acceptor species described herein can be attached to the surface of such a microbubble in any manner not inconsistent with the objectives of the present invention. In some cases, for instance, a donor and/or acceptor species is attached to the exterior surface of a commercially available microbubble using one or more of a carbodiimide, maleimide, or biotin-streptavidin coupling scheme.

In addition, in some embodiments, a fluorophore described herein comprises a thermoresponsive polymer. A "thermoresponsive" polymer, for reference purposes herein, comprises a polymer having a physical or chemical property that changes in a temperature-dependent manner, wherein the change is a discontinuous or binary change. For example, in some cases, the physical conformation or polarity of a thermoresponsive polymer changes in a temperature-dependent manner, and the thermoresponsive polymer exhibits a first conformation below a threshold temperature and a second, substantially different conformation above the threshold temperature. In some embodiments, for instance, a thermoresponsive polymer exhibits an expanded coil or chain confirmation below a threshold temperature and exhibits a compact or globular conformation above the threshold temperature. In some such cases, the threshold temperature can be referred to as the "lower critical solution temperature" (LCST) of the polymer.

Any thermoresponsive polymer not inconsistent with the objectives of the present invention may be used. In some embodiments, a thermoresponsive polymer comprises a poly(N-isopropylacrylamide) or a copolymer of N-isopropylacrylamide with one or more of acrylamide, N-tert-butylacrylamide, acrylic acid, and allylamine. In other cases, a thermoresponsive polymer comprises a poly(N-vinyl-caprolacatam) (PVCL) or a poloxamer such as a Pluronic polymer. Other thermoresponsive polymers may also be used.

Additionally, in some cases, a thermoresponsive polymer of a fluorophore described herein comprises one or more fluorescent moieties or is conjugated to one or more fluorescent species, such as one or more fluorescent dye molecules. The thermoresponsive polymer can be conjugated to the fluorescent species in any manner not inconsistent with the objectives of the present invention. For example, in some cases, a thermoresponsive polymer is coupled to a fluorescent species through one or more covalent bonds such as one or more ester bonds or one or more amide bonds.

FIG. 1 schematically illustrates an ultrasound-switched fluorescence process using a thermoresponsive fluorophore according to one embodiment described herein. As illustrated in FIG. 1, a thermoresponsive polymer is conjugated to a fluorescent species to provide a fluorophore. The fluorophore has a chain conformation and a globular conformation described hereinabove, and the conformation is temperature-dependent. Further, the transition from one conformation to the other results in a change in the fluorescence intensity or lifetime of the fluorescent species. As described further herein, the change in fluorescence intensity or lifetime can be due to differences in the microenvironment of the fluorescent species when the polymer is in the chain conformation compared to the globular conformation. For example, in some cases, the polarity and/or viscosity of the polymer environment experienced by the fluorophore changes depending on whether the polymer is in the chain conformation or the globular conformation.

Further, in some embodiments, a fluorophore described herein comprises a fluorescent material dispersed in and/or attached to the surface of a thermoresponsive polymer nanoparticle. Moreover, the fluorescence properties of the fluorescent material can be dependent on a change of the conformation, polarity, or other physical or chemical property of the polymer nanoparticle. In addition, the property change can be a temperature-dependent change. In this manner, a change in temperature of the thermoresponseive polymer nanoparticle can result in a change in fluorescence intensity and/or lifetime of the fluorescent material, including a change between an on state of the fluorescent material and an off state of the fluorescent material.

For example, in some embodiments, a thermoresponsive polymer nanoparticle can exhibit a temperature-dependent polarity, and the fluorescent material dispersed in the nanoparticle can exhibit a polarity-dependent fluorescence intensity and/or lifetime. Thus, a change in the temperature of the nanoparticle can result in a change in the fluorescence intensity and/or lifetime of the fluorophore.

Figure 2:
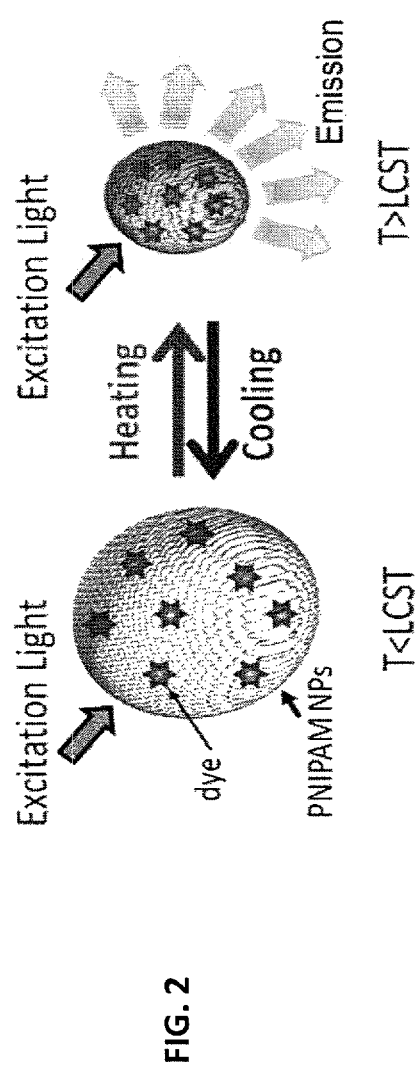
FIG. 2 illustrates an ultrasound-switchable fluorescence process according to one embodiment of a method described herein.

In another exemplary embodiment, a thermoresponsive polymer nanoparticle can have a hydrophilic interior below a threshold temperature and a hydrophobic interior above the threshold temperature. Thus, such a nanoparticle can exhibit a temperature-dependent size when dispersed in a polar or non-polar solvent. For example, when dispersed in water or another polar solvent below the threshold temperature, the nanoparticle can exhibit a larger size due to the presence of water in the hydrophilic interior of the nanoparticle. Similarly, above the threshold temperature, the nanoparticle can exhibit a smaller size due to the exclusion of water from the now hydrophobic interior of the nanoparticle. In this manner, a fluorescent material dispersed in the nanoparticle can have a temperature-dependent concentration, which can result in temperature-dependent fluorescence properties of the overall fluorophore. This process is illustrated schematically in FIG. 2.

A thermoresponsive polymer nanoparticle described herein can have any size or shape not inconsistent with the objectives of the present invention. In some embodiments, for instance, a thermoresponsive polymer nanoparticle is substantially spherical and has a diameter between about 10 nm and about 300 nm, between about 50 nm and about 250 nm, between about 50 nm and about 200 nm, or between about 70 nm and about 150 nm. Other sizes and shapes are also possible.

Further, any fluorescent material not inconsistent with the objectives of the present invention may be dispersed in and/or attached to a thermoresponsive polymer nanoparticle to form a fluorophore described herein. In some embodiments, as described herein, the fluorescent material exhibits a polarity-sensitive fluorescence intensity and/or lifetime. In other cases, the fluorescent material exhibits a temperature-dependent, viscosity-dependent, pH-dependent, and/or an ionic strength-dependent fluorescence intensity and/or lifetime.

Non-limiting examples of fluorescent materials suitable for use in some embodiments described herein include organic dyes such as N,N-dimethyl-4-benzofurazansulfonamide (DBD); 4-(2-Aminoethylamino)-7-(N,N-dimethylsulfamoyl)benzofurazan (DBD-ED); indocyanine green (ICG); a Dylight-700 such as Dylite-700-2B; IR-820; 3,3'-Diethylthiatricarbocyanine iodide (DTTCI); LS-277; LS-288; a cypate; a rhodamine dye such as rhodamine 6G or rhodamine B; or a coumarin. In some instances, a fluorescent material comprises an azadipyrromethene. In addition, in some cases, a fluorescent material comprises an inorganic species such as a semiconductor nanocrystal or quantum dot, including a II-VI semiconductor nanocrystal such as ZnS or CdSe or a III-V semiconductor nanocrystal such as InP or InAs. In other instances, a fluorescent material comprises a Lanthanide species. Other fluorescent materials may also be used.

An ultrasound-switchable fluorophore described herein can have any fluorescence emission profile not inconsistent with the objectives of the present invention. For example, in some embodiments, a fluorophore exhibits an emission profile including visible light or centered in the visible region of the electromagnetic spectrum, such as between 450 nm and 750 nm. In some cases, a fluorophore exhibits an emission profile including infrared (IR) light or centered in the IR region of the electromagnetic spectrum. For example, in some instances, a fluorophore described herein exhibits an emission profile centered in the near-IR (NIR, 750 nm-1.4 μm), short-wavelength IR (SWIR, 1.4-3 μm), mid-wavelength IR (MWIR, 3-8 μm), or long-wavelength IR (LWIR, 8-15 μm). Moreover, in some embodiments, a fluorophore described herein has an emission profile overlapping with a wavelength at which water and/or biological tissue has an absorption minimum, such as a wavelength between about 700 nm and about 800 nm or between about 1.25 μm and about 1.35 μm. Additionally, in some cases, a population of ultrasound-switchable fluorophores described herein comprises fluorophores having differing emission profiles. For example, in some cases, a first fluorophore of the population can emit in the NIR and a second fluorophore of the population can emit in the visible region of the electromagnetic spectrum. In this manner, multiplexed imaging can be achieved.

Further, in some instances, a fluorophore described herein exhibits a fluorescence lifetime of at least about 1 ns, at least about 3 ns, or at least about 10 ns. In some embodiments, a fluorophore described herein exhibits a fluorescence lifetime between about 1 ns and about 15 ns, between about 1 ns and about 10 ns, between about 1 ns and about 4 ns, between about 3 ns and about 7 ns, between about 3 ns and about 5 ns, or between about 10 ns and about 15 ns.

Additionally, in some embodiments, an ultrasound-switchable fluorophore described herein exhibits one or more desirable features related to the on and off states of the fluorophore. For example, in some cases, a fluorophore exhibits a high on-to-off ratio in fluorescence intensity ($I_{On}/I_{Off}$), a high on-to-off ratio in fluorescence lifetime ($T_{On}/T_{Off}$), a sharp transition bandwidth between on and off states ($T_{BW}$), and/or an adjustable switching threshold ($S_{th}$), such as an adjustable switching threshold temperature ($T_{th}$) or an adjustable switching threshold pressure ($P_{th}$). These metrics can be further described with reference to FIG. 3.

Figure 3:
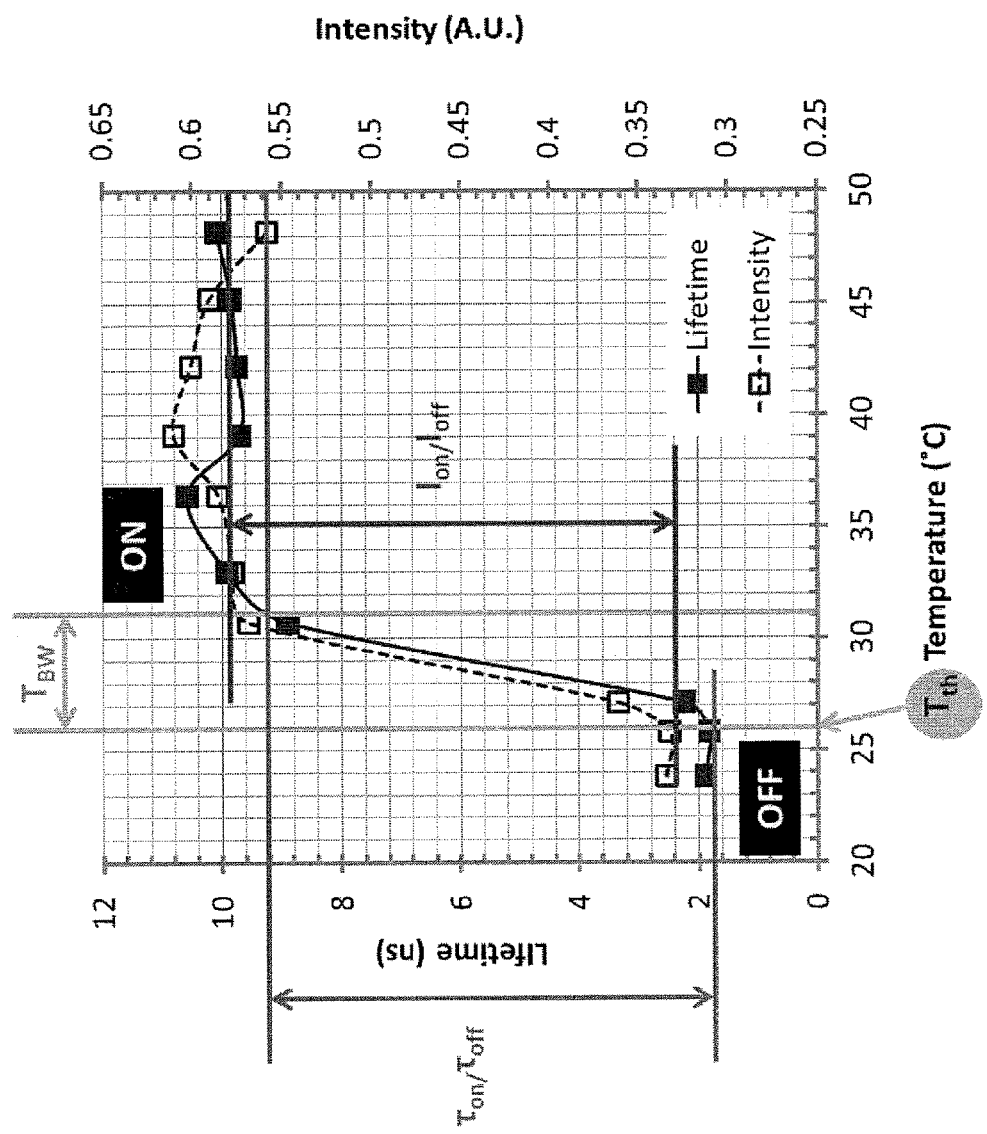
FIG. 3 illustrates plots of the fluorescence intensity and fluorescence lifetime of a temperature-dependent fluorophore suitable for use in some embodiments of methods described herein.

FIG. 3 illustrates plots of the fluorescence intensity and fluorescence lifetime of a temperature-dependent fluorophore as a function of temperature. However, it is to be understood that the same principles and nomenclature can be applied in an analogous way for a fluorophore that exhibits pressure-dependent fluorescence or fluorescence dependent on some other variable described herein. In such an instance, the temperature axis of FIG. 3 could be replaced by a pressure axis or an axis corresponding to another variable related to fluorescence switching without otherwise substantially altering the appearance of FIG. 3. With reference to FIG. 3, $T_{th}$ refers to the switching threshold temperature. $I_{On}/I_{Off}$ refers to the ratio of the average fluorescence intensity of the fluorophore over a range of temperatures above the threshold temperature to the average fluorescence intensity of the fluorophore over a range of temperatures below the threshold temperature. Similarly, $\tau_{On}/\tau_{Off}$ refers to the ratio of the average fluorescence lifetime of the fluorophore over a range of temperatures above the threshold temperature to the average fluorescence lifetime of the fluorophore over a range of temperatures below the threshold temperature. In some embodiments, the averages are taken over a range of temperatures having a magnitude that is about 5 percent to about 100 percent of the magnitude of the switching threshold value but that lie outside of the transition bandwidth $T_{BW}$. $T_{BW}$ refers to the range of temperature values (or, analogously, pressure or other variable values) over which the fluorphore switches from the on state to the off state in the manner of a step function. In other words, $T_{BW}$ refers to the width of the step between the on and off states. The smaller the $T_{BW}$, the more the fluorescence intensity profile of the fluorophore resembles a true step function having a discontinuity between the on state and the off state. In FIG. 3, the $I_{On}$ value is taken as the average intensity over a temperature range of about 33° C. to about 48° C. (a range of about 16° C., or about 62 percent of the $T_{th}$ value of 26° C.) and the $I_{Off}$ value is taken as the average intensity over a temperature range of about 23° C. to about 25° C. (a range of about 3° C., or about 12 percent of the $T_{th}$ value of 26° C.). In general, the range of temperature values used for determining the average fluorescence intensity in the on and off states can be based on the range of temperature values of interest for a particular imaging application. An ultrasound-switchable fluorophore described herein can exhibit any of the $I_{On}/I_{Off}$, $\tau_{On}/\tau_{Off}$, $T_{BW}$, and $T_{th}$ values provided hereinbelow in Table 1.

TABLE 1

| $I_{On}/I_{Off}$ | $\tau_{On}/\tau_{Off}$ | $T_{BW}$ (° C.) | $T_{th}$ (° C.) |
|---|---|---|---|
| >2 | ≥2 | <15 | >25 |
| >3 | ≥3 | <10 | >30 |
| >5 | ≥5 | ≤5 | >37 |
| >8 | 2-10 | 1-15 | ≥40 |
| 2-10 | 2-7 | 1-10 | 20-45 |
| 3-10 | 2-5 | 3-12 | 25-35 |
| 3-9 | 3-7 | 3-10 | 37-45 |
| 5-9 | 3-5 | 3-5 | 38-45 |

Methods of imaging described herein, in some embodiments, also comprise exposing a biological environment to a pulsed beam of electromagnetic radiation, including prior to exposing the biological environment to an ultrasound beam. The pulsed beam of electromagnetic radiation can have a picosecond pulse duration, such as a pulse duration of no greater than 100 ps, wherein the pulse duration is defined as the FWHM of the optical power of the pulsed beam over time. The pulsed beam can have any wavelength and power not inconsistent with the objectives of the present invention. In some cases, for instance, the wavelength of the pulsed beam is selected to substantially overlap with the absorption profile of one or more species present in the biological environment, as further described hereinabove. In some embodiments, the pulsed beam has a visible wavelength or a NIR wavelength. Other pulsed beams may also be used.

Methods of imaging described herein also comprise exposing a biological environment to one or more ultrasound beams to create an activation region within the biological environment. The ultrasound beam can have any ultrasound frequency not inconsistent with the objectives of the present invention. In some embodiments, an ultrasound beam comprises an oscillating sound pressure wave with a frequency of greater than about 20 kHz or greater than about 2 MHz. In some cases, an ultrasound beam described herein has a frequency of up to about 5 GHz or up to about 3 GHz. In some embodiments, an ultrasound beam has a frequency between about 20 kHz and about 5 GHz, between about 50 kHz and about 1 GHz, between about 500 kHz and about 4 GHz, between about 1 MHz and about 5 GHz, between about 2 MHz and about 20 MHz, between about 2 MHz and about 10 MHz, between about 5 MHz and about 200 MHz, between about 5 MHz and about 15 MHz, between about 200 MHz and about 1 GHz, between about 500 MHz and about 5 GHz, or between about 1 GHz and about 5 GHz.

In addition, an ultrasound beam can have any power not inconsistent with the objectives of the present invention. In some embodiments, for instance, an ultrasound beam has a power between about 0.1 W/cm$^2$ and about 10 W/cm$^2$, between about 0.1 W/cm$^2$ and about 5 W/cm$^2$, between about 0.5 W/cm$^2$ and about 5 W/cm$^2$, between about 1 W/cm$^2$ and about 10 W/cm$^2$, or between about 1 W/cm$^2$ and about 5 W/cm$^2$. In other cases, an ultrasound beam has a power between about 100 W/cm$^2$ and about 5000 W/cm$^2$, or between about 100 W/cm$^2$ and about 3000 W/cm$^2$. In some cases, the use of an ultrasound beam having a high power, such as a power described herein, can result in the generation of non-linear effects within the activation region. Moreover, in some embodiments, the effective size of the activation region can be reduced in this manner, leading to improved imaging resolution.

A biological environment can be exposed to an ultrasound beam in any manner not inconsistent with the objectives of the present invention. For example, in some embodiments, a biological environment is exposed to an ultrasound beam described herein for only a limited duration. In some cases, for instance, the ultrasound beam is provided to the biological environment for less than about 1 second or less than about 500 ms. In some embodiments, the ultrasound beam is provided to the biological environment for less than about 300 ms, less than about 100 ms, less than about 50 ms, or less than about 10 ms. In some cases, the ultrasound beam is provided to the biological environment for about 1 ms to about 1 second, about 1 ms to about 500 ms, about 1 ms to about 300 ms, about 1 ms to about 100 ms, about 1 ms to about 50 ms, about 1 ms to about 10 ms, about 10 ms to about 300 ms, about 10 ms to about 100 ms, about 10 ms to about 50 ms, or about 50 ms to about 100 ms. The use of short exposure times of a biological environment to an ultrasound beam, in some embodiments, can permit the time-gating of fluorescence signals, such that a desired USF signal can be temporally separated from one or more undesired or non-analyte fluorescence signals, such as a tissue autofluorescence signal or a signal from a randomly switched-on fluorophore.

Moreover, the ultrasound beam can be a continuous wave beam or a pulsed or modulated beam. The use of a modulated or pulsed ultrasound beam, in some embodiments, can further improve the SNR of a method described herein by permitting frequency-gated detection of the USF signal. For example, in some cases, a pulsed or modulated ultrasound beam provides an ultrasound exposure having a specific frequency or modulation. As a result, the corresponding USF signal can also exhibit the same specific frequency or modulation. Thus, in some such cases, a lock-in amplifier is used to increase the sensitivity of the detector to the specific frequency or modulation, thus increasing the overall sensitivity and SNR of the method.

In some embodiments of methods described herein, a single ultrasound beam is directed toward the biological environment using a single ultrasound transducer, such as a high intensity focused ultrasound (HIFU) transducer. In other instances, a plurality of ultrasound beams is directed toward the biological environment using a plurality of ultrasound transducers. Moreover, in some cases, a first ultrasound beam is directed toward the biological environment at a first angle and/or from a first direction, and a second ultrasound beam is directed toward the biological environment at a second angle and/or from a second direction differing from the first angle and/or direction. In some embodiments, for instance, the first and second directions are orthogonal or substantially orthogonal directions, such as directions separated by 80 to 100 degrees. In other cases, the directions are separated by less than 80 degrees or more than 100 degrees. Further, if desired, additional ultrasound beams may also be directed toward the biological environment from additional directions or at additional angles. In such cases, the focal zones of the beams can overlap or intersect with one another to form an activation region at the intersection of the beams. In this manner, an activation region can have a smaller volume or cross section than the focal zone or cross section of a single ultrasound beam used to generate the activation region, thereby improving imaging resolution. In some cases, for instance, the activation region has a lateral dimension and/or an axial dimension of less than about 2 mm, less than 1.5 mm, or less than about 1 mm. In some embodiments, the activation region has a lateral dimension and/or an axial dimension of less than about 700 μm or less than about 500 μm. In some embodiments, the activation region has a lateral dimension and/or an axial dimension of about 300 μm to about 2 mm, about 400 μm to about 1.5 mm, about 400 μm to about 1 mm, about 400 μm to about 700 μm, or about 400 μm to about 500 μm. In some cases, the lateral and axial dimensions both have a size recited herein, including a size below about 1 mm or below about 700 μm. Moreover, in some embodiments, the lateral and axial dimensions of the activation region are different, thereby providing a relatively anisotropic activation region. Alternatively, in other instances, the lateral and axial dimensions are substantially the same, thereby providing a relatively "square" or isotropic activation region.

An "activation region," for reference purposes herein, comprises a region of the biological environment in which ultrasound-switchable fluorophores described herein can be switched from an off state to an on state. For example, in some cases, an activation region comprises a region of negative pressure compared to other portions of the biological environment. Similarly, in other instances, an activation region comprises a high temperature region. As described further herein, the temperature, pressure, or other characteristic of an activation region described herein can be selected based on the switching threshold of a fluorophore disposed in the biological environment. For example, in some cases, one or more ultrasound beams are configured to form an activation region having an average temperature or a maximum temperature greater than about 30° C., greater than about 35° C., or between about 30° C. and about 50° C. In other embodiments, an activation region has an average negative pressure or a maximum negative pressure between about 10 kPa and about 150 kPa or between about 80 kPa and about 120 kPa. Moreover, as described further herein, the size, shape, and/or other properties of the activation region can be determined by the number and/or power of the one or more ultrasound beams used to form the activation region. In some cases, for instance, the size and shape of an activation region is defined by the focal zone of a single ultrasound beam. In other cases, an activation region is defined by the overlap of the focal zones of a plurality of ultrasound beams.

Methods of imaging described herein also comprise exciting at least one fluorophore in an on state with a beam of electromagnetic radiation and detecting light emitted by the at least one fluorophore. A fluorophore can be excited with a beam of electromagnetic radiation in any manner not inconsistent with the objectives of the present invention. In some embodiments, for instance, a fluorophore is excited using a laser excitation source such as a diode laser. In other instances, a fluorophore is excited using one or more light emitting diodes (LEDs) or a broadband excitation source. Moreover, an excitation source described herein can provide any wavelength of light not inconsistent with the objectives of the present invention. In some embodiments, a fluorophore described herein is excited with a beam of electromagnetic radiation comprising visible light, NIR light, or IR light. In other cases, the beam of electromagnetic radiation comprises ultraviolet (UV) light.

Similarly, light emitted by the fluorophore can be detected in any manner not inconsistent with the objectives of the present invention. In some embodiments, for example, detecting light emitted by at least one fluorophore in an on state comprises detecting the light in a time-gated or frequency-gated manner, including a time-gated manner or frequency-gated manner described herein. In some cases, the light emitted by the at least one fluorophore in the on state is detected after a time delay that is longer than the fluorescence lifetime of the fluorophore in the off state or longer than the fluorescence lifetime of another species present in the biological environment. For example, in some embodiments, the light emitted by the at least one fluorophore in the on state is detected after a time delay that is longer than the autofluorescence lifetime of a non-fluorophore species present in the biological environment, such as the autofluorescence lifetime of tissue, which may be up to about 4 ns or up to about 5 ns. In addition, any detector not inconsistent with the objectives of the present invention may be used. In some embodiments, for instance, one or more photomultiplier tube (PMT) detectors can be used. Other configurations are also possible.

In addition, methods described herein, in some embodiments, can exhibit improved penetration depth/resolution ratios (DRRs). The "penetration depth" of an imaging method, for reference purposes herein, is defined as the depth below the surface of an imaged object at which the intensity of the ultrasound beam inside the object falls to 1/e (about 37 percent) of its initial value at the surface. The "resolution" of a method, for reference purposes herein, is the microscopic resolution (i.e., the size at which separate objects can be distinguished), which is taken to be equal to the FWHM of the activation region in a given dimension. In some embodiments, a method described herein exhibits a DRR of at least about 100. In other cases, a method described herein exhibits a DRR of at least about 200, at least about 300, or at least about 400. In some embodiments, a method described herein exhibits a DRR of up to about 500. In some cases, a method described herein exhibits a DRR between about 100 and about 500, between about 100 and about 400, between about 100 and about 300, or between about 200 and about 500. Further, the penetration depth of a method described herein, in some embodiments, can be up to 100 mm, up to 50 mm, or up to 30 mm. In some cases, the penetration depth is between about 10 mm and about 100 mm, between about 10 mm and about 60 mm, between about 10 mm and about 50 mm, between about 20 mm and about 90 mm, or between about 20 mm and about 50 mm. In addition, the resolution of a method described herein, in some embodiments, is less than about 100 μm, less than about 70 μm, less than about 50 μm, or less than about 30 μm. In some cases, the resolution is between about 10 μm and about 100 μm, between about 10 μm and about 70 μm, between about 10 μm and about 50 μm, between about 10 μm and about 30 μm, between about 20 μm and about 100 μm, between about 20 μm and about 80 μm, between about 20 μm and about 50 μm, or between about 30 μm and about 70 μm.

It is to be understood that a method of imaging described herein can include any combination of steps described herein and use any combination of equipment and materials described herein not inconsistent with the objectives of the present invention. For example, in some cases, a method described herein comprises disposing a fluorophore comprising a thermoresponsive polymer in deep biological tissue, forming an activation region using two orthogonal HIFU transducers, and detecting emission from the fluorophore in a time-gated manner, thereby providing a DRR greater than about 200. Other combinations and configurations are also possible.

Some embodiments described herein are further illustrated in the following non-limiting examples.

Example 1

Ultrasound-Switchable Fluorophores

General

A series of ultrasound-switchable fluorophores or contrast agents suitable for use in methods of imaging according to some embodiments described herein was prepared by encapsulating an environment-sensitive NIR dye, indocyanine green (ICG), into thermoresponsive polymer nanoparticles (NPs). The NPs can be disposed in an aqueous environment such as a biological environment described herein. When the environment's temperature is below a threshold temperature (which can be referred to as LCST of the NPs), the NPs are hydrophilic and absorb a large amount of water, with the result that the NPs have a relatively large average diameter. Not intending to be bound by theory, it is believed that ICG molecules fluoresce weakly in water-rich microenvironments because water provides a polar and nonviscous microenvironment and thereby increases the nonradiative decay rate of the excited ICG molecules. When the temperature increases above the threshold temperature, the NPs become hydrophobic, causing expulsion of water from the NPs and a corresponding reduction in average NP diameter. Again not intending to be bound by theory, it is believed that the ICG molecules dispersed within the NPs are thus exposed to a polymer-rich microenvironment having a relatively low polarity and high viscosity compared to the water-rich microenvironment. It is believed that such a low polarity, high viscosity microenvironment can suppress the nonradiative decay rate of the excited ICG molecules, resulting in an increase in the fluorescence intensity of the ICG. It was observed that this fluorescence switching behavior from an off state to an on state was reversible and repeatable. In particular, a high intensity focused ultrasound (HIFU) transducer could be used to reversibly and repeatedly switch the fluorophores between on and off states by altering the temperature in the transducer's focal zone above and below the LCST of the NPs.

Figure 4:
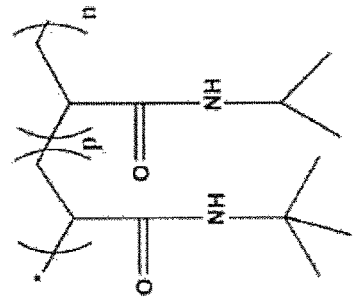
FIG. 4 illustrates the structures of components of fluorophores suitable for use in some embodiments of methods described herein.
Figure 4:
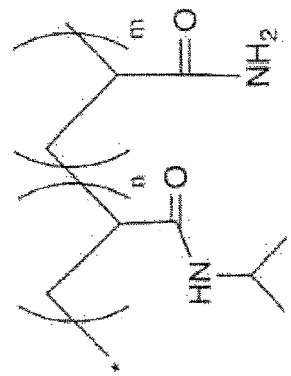
Figure 4:
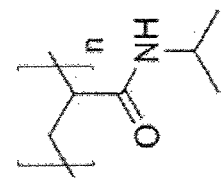
Figure 4:
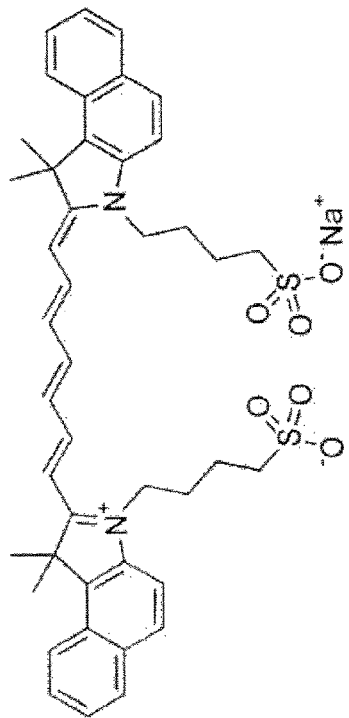

The NPs were formed from thermoresponsive polymers of either poly (N-isopropylacrylamide) (PNIPAM) or its copolymer with acrylamide (AAm) or N-tert-butylacrylamide (TBAm). FIG. 4 illustrates the structures of such polymers and ICG. Specifically, four types of polymer NPs were synthesized, including (1) ICG-encapsulated P(NIPAM-TBAm185:15) NPs, (2) ICG-encapsulated PNIPAM NPs, (3) ICG-encapsulated P(NIPAM-AAm 90:10) NPs, and (4) ICG-encapsulated P(NIPAM-AAm 86:14) NPs. The ratios in the foregoing formulas refer to the molar ratio between the monomer of NIPAM and the monomer of TBAm or AAm used to form the NPs. The LCST of these thermoresponsive polymer NPs could be altered based on the amount of AAm and/or TBAm copolymerized with PNIPAM. For example, using a hydrophilic monomer (such as AAm) resulted in a polymer having a higher LCST. In contrast, using a hydrophobic monomer (such as TBAm) decreased the LCST. In addition, it should be noted that TBAm is more hydrophobic than NIPAM, while AAm is more hydrophilic than NIPAM.

Materials

N-isopropylacrylamide (NIPAM), acrylamide (AAm), ammonium persulfate (APS), sodium dodecyl sulfate (SDS), N,N,N',N'-tetramethyl ethylene diamine (TEMED), N,N'-methylenebisacrylamide (BIS), N-tert-butylacrylamide (TBAm), sodium ascorbate, and ICG were purchased from Sigma-Aldrich (St. Louis, Mo., USA). All chemicals were used as received without further purification.

Synthesis

The ICG-containing PNIPAM NPs were prepared as follows. Other NPs were prepared using a similar protocol, except with the addition of appropriate amounts of TBAm and/or AAm monomers. In addition, it was also possible to partially or completely replace TBAm and/or AAm with one or more of acrylic acid (AAc) and allylamine (AH) to form other copolymers of NIPAM, such as P(NIPAM-AAc), P(TBAm-NIPAM-AAc), or P(NIPAM-AH).

Briefly, to prepare PNIPAM NPs, NIPAM (monomer, 0.6822 g), BIS (cross linker, 0.0131 g), and SDS (surfactant, 0.0219 g) were dissolved in 50 mL deionized water in a 250 mL Schlenk tube, followed by purging with nitrogen for 10 minutes. ICG (fluorophore, 0.0034 g), APS (initiator, 0.039 g), and TEMED (accelerator, 51 μL) were then added into the tube. The tube was then placed under an inert nitrogen atmosphere by three cycles of applying vacuum on a Schlenk line followed by backfilling with nitrogen. The contents of the flask were then stirred at room temperature for 4 hours. The reaction was stopped by exposing the flask contents to air. The product was dialyzed against deionized water using a 10-kDa molecular weight cutoff membrane for 3 days to remove extra surfactants and unreacted materials. The composition of the final product was confirmed with a Fourier transform infrared (FTIR) spectrometer (Thermo Nicolet 6700, West Palm Beach, Fla., USA), at 4,000 to 600 $cm^{-1}$.

The diameter of the NPs was measured by dynamic light scattering (DLS) and transmission electron microscopy (TEM). TEM was also used to determine the morphology of the NPs. For DLS measurements, 200 μL of the product was diluted with 2.8 mL of deionized water and then analyzed at room temperature (25° C.) with a Nanotrac 150 (Microtrac, Inc., Nikkiso, San Diego, Calif., USA). For TEM measurements, samples were prepared by drop casting an aqueous dispersion of product NPs (at about 1 mg/mL) onto a carbon-coated copper grid (FF200-Cu-50, Electron Microscopy Sciences, Hatfield, Pa., USA), followed by staining with 0.2% uranyl acetate. TEM experiments were carried out using a JEOL 1200 EX TEM (JEOL, Peabody, Mass., USA). The NPs had sizes between 70 nm and 150 nm, based on dynamic light scattering (DLS) and transmission electron microscopy (TEM). In particular, when measured by DLS, (1) ICG-containing PNIPAM NPs had an average size of 150±25 nm; (2) ICG-containing P(NIPAM-TBAm 185:15) NPs had an average size of 76±4 nm; (3) ICG-containing P(NIPAM-AAm 86:14) NPs had an average size of 75±25 nm; and (4) ICG-containing P(NIPAM-AAm 90:10) NPs had an average size of size of 76±2 nm. The sizes measured by DLS were somewhat larger than the sizes measured by TEM due to the presence of surfactant (SDS) and hydration layers around the NPs in aqueous solution. For example, the average size of the NPs of sample (1) above was approximately 110 nm when measured by TEM. The NPs were nearly spherical.

Figure 5:
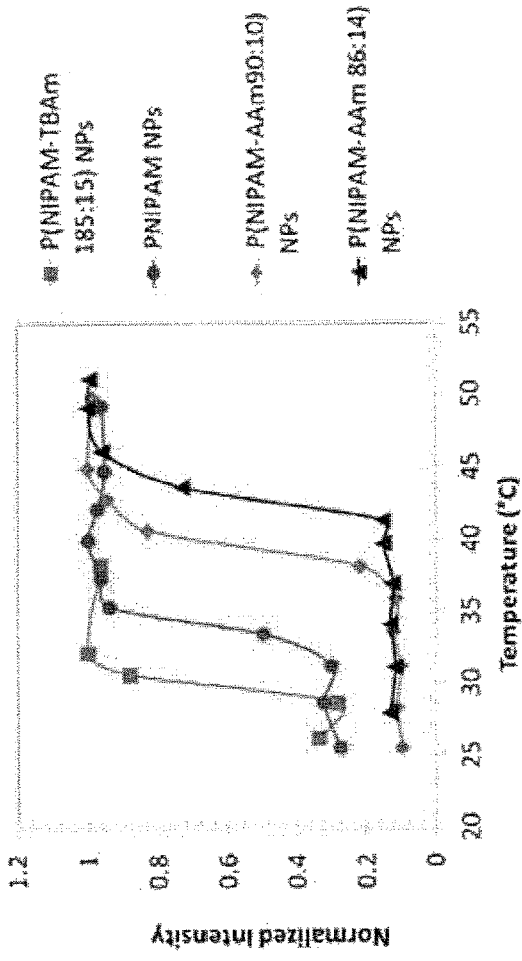
FIG. 5 illustrates fluorescence switching curves of fluorophores suitable for use in some embodiments of methods described herein.
Figure 6:
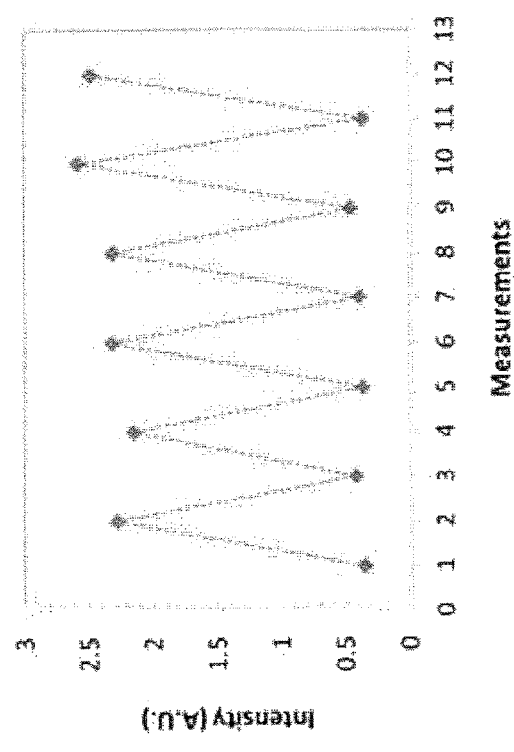
FIG. 6 illustrates fluorescence data for a fluorophore suitable for use in some embodiments of methods described herein.

The fluorescence switching curves of the polymer NPs are shown in FIG. 5. The fluorescence intensity is plotted as a function of the sample temperature. The sharp switching features can be clearly seen for all four NPs, with switching threshold temperatures (LCSTs or $T_{th}$'s) of 28° C., 31° C., 37° C., and 41° C. Further, switching was observed multiple times in a single sample. For example, FIG. 6 illustrates fluorescence data for ICG-containing P(NIPAM-AAm 90:10) NPs at 12 different time points (measurement points 1-12 on the x-axis) cycling between low temperature (25° C., measurement points 1, 3, 5, 7, 9, and 11) and high temperature (44° C., measurement points 2, 4, 6, 8, 10, and 12). In addition, the $I_{On}/I_{Off}$ ratio reached 3.3, 2.9, 9.1, and 9.1, respectively, for samples (1), (2), (3), and (4). These values are at least 1.6 to 5.1 times higher than that of some other contrast agents.

Figure 7:
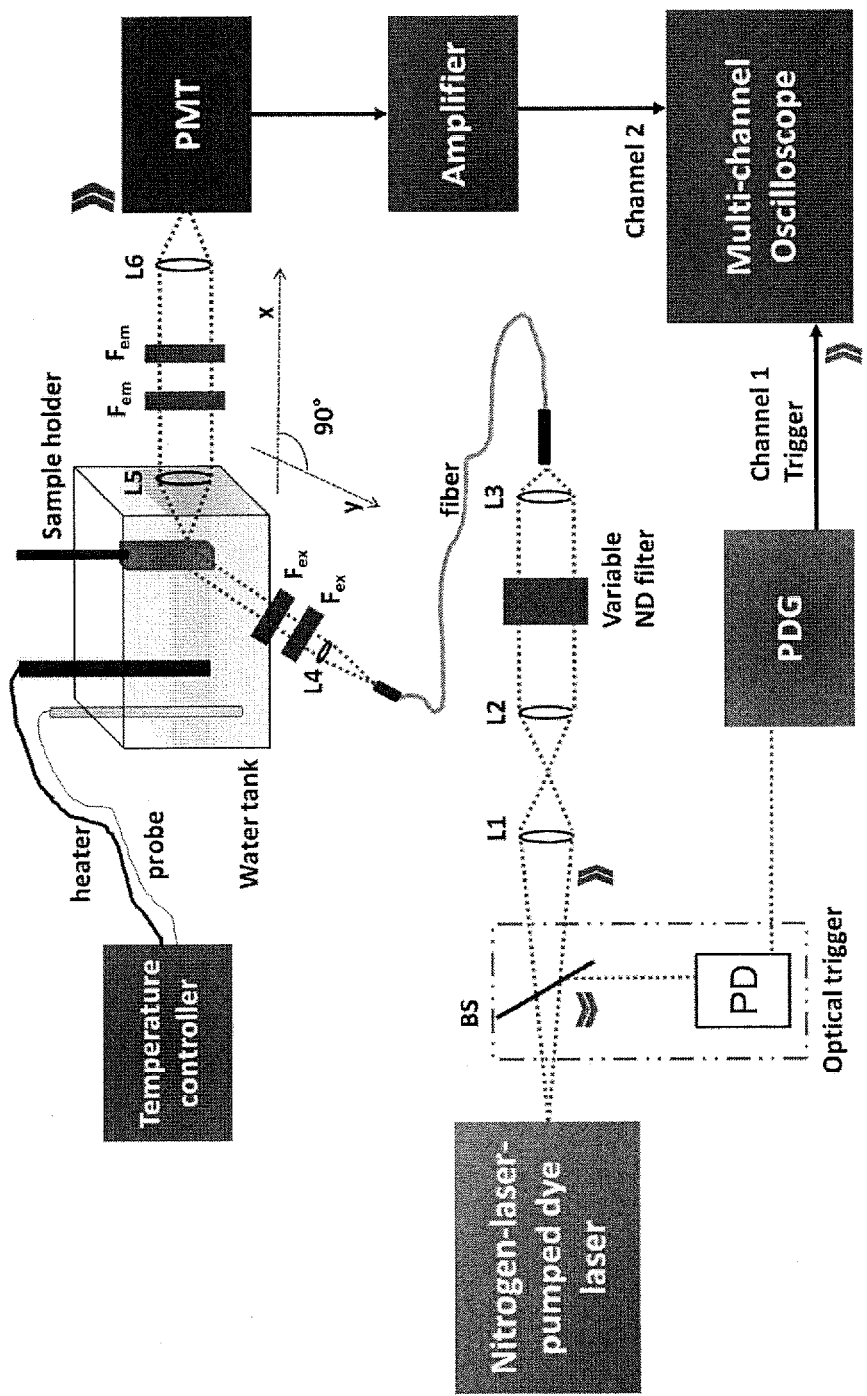
FIG. 7 illustrates a system used to measure the fluorescence characteristics of fluorophores suitable for use in some embodiments of methods described herein.

The system used to measure the fluorescence characteristics of fluorophores described herein is illustrated schematically in FIG. 7. In general, the emission pulses of fluorophores were averaged 100 times and the averaged peak value was used to represent the fluorescence intensity. As illustrated in FIG. 7, "$F_{ex}$" refers to an excitation filter; "$F_{em}$" refers to an emission filter; "L" refers to a lens; "PMT" refers to a photomultiplier tube; "BS" refers to a beam splitter; "PD" refers to a photodiode; "PDG" refers to a pulse-delay generator; and "ND filter" refers to a natural density filter.

Example 2

Methods of Imaging Using Thermoresponsive Polymer Nanoparticles

General

Figures 8A, 8B, 8C:
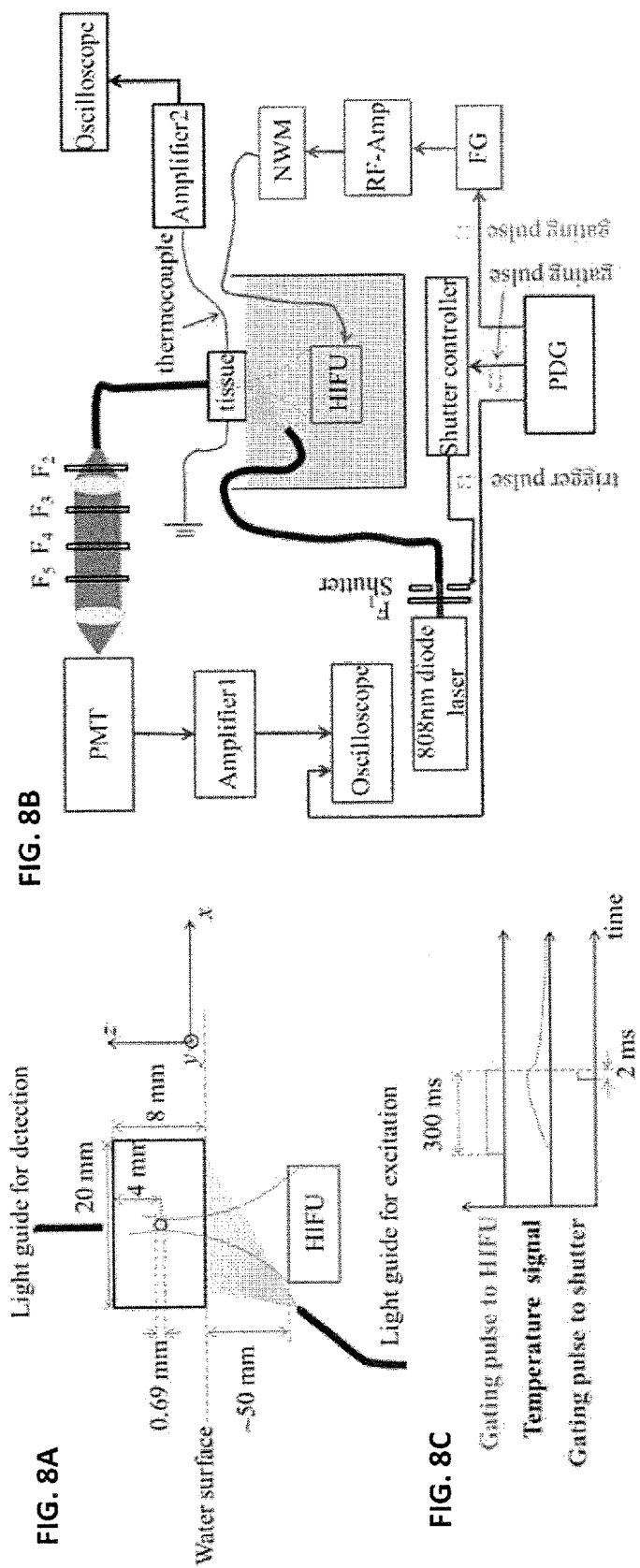
FIG. 8A illustrates components and steps of a method of imaging according to one embodiment described herein.
FIG. 8B illustrates components and steps of a method of imaging according to one embodiment described herein.
FIG. 8C illustrates steps of a method of imaging according to one embodiment described herein.

Methods of imaging according to some embodiments described herein were carried out as follows. First, a small silicone tube (with a mean diameter of 0.69 mm; Instech Lab, BSILT031, PA, USA) was filled with an aqueous solution of the ICG-containing PNIPAM NPs (LCST=31° C.) of Example 1. The tube was then embedded in a piece of porcine muscle tissue to simulate a blood vessel as a target for USF imaging. FIG. 8A schematically illustrates the configuration of the tissue sample, the tube, the excitation light source, the fluorescence collection fiber, and the HIFU transducer used for imaging. The porcine tissue had a thickness of approximately 8 mm (in the z-direction of FIG. 8A) and a width of approximately 20 mm (in the x-direction). The tube was inserted into the tissue along the y direction. The distance from the tube center to the top surface of the tissue was approximately 4 mm. A fiber bundle with a diameter of approximately 3 mm (Edmund Optics NT39-366, New Jersey, USA) was used to deliver the excitation light from a laser to the bottom of the tissue to excite fluorophores switched to the on state by exposure to the HIFU beam. A second fiber bundle (Edmund Optics NT42-345) was placed on the top of the tissue to collect USF photons. A 2.5 MHz HIFU transducer (H-108, Sonic Concepts, Washington, USA; active diameter: 60 mm; focal length: 50 mm) was positioned at the bottom of the tissue and focused on the tube region. To efficiently transmit the acoustic energy into the tissue, the HIFU transducer, the bottom surface of the tissue sample, and the fiber bundle for delivering the excitation light were submerged in water. For imaging the tube two-dimensionally, the HIFU transducer was scanned or translated in the x-y plane.

USF Imaging System

The setup of the USF imaging system is illustrated schematically in FIG. 8B. The system included four primary subsystems: (1) an optical subsystem, (2) an ultrasonic subsystem, (3) a temperature measurement subsystem, and (4) an electronic control subsystem. The optical subsystem included components for the delivery of the excitation light or beam of electromagnetic radiation and the collection of the emission light. The excitation light was generated using an 808 nm diode laser (MDL-III-808R) and was delivered to the bottom of the sample tissue via the fiber bundle described above. A band pass filter F1 (FF01-785/62-25, Semrock, N.Y.; central wavelength: 785 nm; bandwidth: 62 nm) was used as an excitation filter to clean up any undesirable sideband components of the diode laser located in the pass band of the emission filters. The laser was operated in a continuous wave (CW) mode; however, the sample illumination times and durations were controlled using a fast mechanical shutter (UNIBITZ LS3T2, New York) that was triggered by a pulse delay generator (PDG, P400, Highland, Calif.). The shutter had a response time of 0.5 ms. Alternatively, it is also possible to use a pulse laser rather than a CW laser. The emitted photons collected via the second fiber bundle described above were delivered to a set of emission filters and then received by a photomultiplier tube (PMT). The combination of four emission filters permitted maximum rejection of the excitation photons and passing of the fluorescence emission photons. Specifically, two long pass interference filters (F2 and F5; BLP01-830R-25, Semrock, N.Y., USA; edge wavelength: 846 nm) and two long pass absorptive glass filters (F3 and F4; FSR-RG830, Newport, Irvine, Calif., USA, cut-on 830 nm) were positioned as illustrated in FIG. 8B. Two NIR achromatic doublet lenses (AC-254-035-B, Thorlabs, N.J., USA) were used to collimate the fluorescence photons for best rejecting the excitation photons by the interference filters and to focus the filtered photons onto a cooled and low-noise PMT (H7422P-20 driven by a high-voltage source C8137-02, Hamamatsu, Japan). The signal was further amplified by a low-noise current preamplifier (SR570, Stanford Research Systems, Calif., USA) and acquired by a multichannel oscilloscope (DPO4102B-L, Tektronix, Oreg., USA).

The ultrasonic subsystem included the HIFU transducer described above, various driving components, an impedance matching network (NWM), a radio-frequency (RF) power amplifier, and a function generator (FG). Specifically, a gated sinusoidal wave signal with a central frequency of 2.5 MHz was generated by the FG (33220A, Agilent, Calif., USA) and was further amplified by the RF power amplifier (325LA, E&I, New York, USA). The amplified signal was input into the NWM to drive the HIFU transducer. The HIFU transducer was focused on the silicone sample tube. The HIFU transducer was mounted on a two-dimensional translation stage for both initial HIFU positioning and subsequent scanning. In the initial positioning, the HIFU transducer was moved to the position where the temperature signal from the thermocouple reached its maximum (indicating that the thermocouple junction was located on the HIFU focus). This position was considered to be the center of the image. A rectangular area (4.0 mm×1.02 mm) was raster scanned by the HIFU transducer surrounding the center. The entire ultrasonic subsystem was controlled by the PDG, including the firing of the HIFU pulse, the firing of the excitation light pulse, and the data acquisition of the oscilloscope. The time sequence of these processes is plotted in FIG. 8C. In this Example, the ultrasonic exposure time was 300 ms, determined by the width of the gating pulse from the PDG.

To appropriately synchronize the laser pulse, fluorescence signal, and data acquisition, the following strategies were adopted. The laser pulse was delayed approximately 100 ns by coupling the laser beam into a 20 m optical fiber (FT200EMT, Thorlabs Inc., Newton, N.J., USA). When an excitation light pulse was fired by the laser, a small amount of laser energy was split by a beam splitter and delivered to a fast photodiode (PD) to generate an electronic pulse. This pulse was used to trigger the PDG. The output of the PDG was used to trigger the oscilloscope for data acquisition. The triggering time was adjusted by controlling the output delay time of the PDG. Thus, the data acquisition of the oscilloscope was well synchronized and matched with the fluorescence signal. The 100 ns delay from the laser pulse was large enough to account for the total electronic delay of the trigger signal.

The temperature at the HIFU focus was measured by a micron-sized thermocouple via an amplifier and a second oscilloscope. Specifically, a thermocouple with a small junction size of 75 μm (CHCO003, Omega Engineering, Connecticut, USA) was disposed in the silicone tube to measure HIFU-induced temperature changes. The junction was fixed at the center of the scanning area. The output voltage signal from the thermocouple was amplified by an amplifier circuit including a high-precision operational amplifier OPA2277 and acquired by an oscilloscope (Infiniium 54830D MSO, Agilent, Calif., USA). By scanning the HIFU transducer along the x direction, the temperature profile was acquired. The thermocouple signal was found to be linearly proportional to the temperature, which was previously calibrated outside the tissue sample before the test. The measured peak temperature at the HIFU focus was found to be approximately 45° C.

During the ultrasonic exposure period, the tissue temperature at the HIFU focus increased continuously. After the exposure, the temperature decreased as a result of thermal diffusion. The excitation light illuminated the tissue for the final 2 ms right before the end of the ultrasonic exposure, and illumination was initiated by opening the shutter. At the same time, the fluorescence signal was acquired by the oscilloscope, which was triggered by a pulse from the PDG. The HIFU transducer was scanned or translated using a two-dimensional translation stage.

High Resolution USF Images

The HIFU transducer described above was used to ultrasonically image the sample tube in the tissue sample descried above. A pulser/receiver (5073 PR, Olympus NDT, USA) was used for both exciting the transducer and receiving the reflected acoustic echoes. The NWM was also used for impedance matching between the transducer and the pulser/receiver. The reflected acoustic signal was amplified by the pulser/receiver and acquired by a digitizer (NI USB 5133) interfaced to a computer. Such a received signal is usually called an A-line in the ultrasound imaging field and represents the tissue acoustic impendence distribution along the depth (z) direction. One A-line was acquired at each location in the x-y plane. By scanning the HIFU transducer in the x-y plane, a set of three-dimensional (x, y, and z) data was acquired. The envelope of each A-line was calculated for forming the C-mode images at different depths. To compare with the USF image, a set of two-dimensional data in the x-y plane (one of the C-mode images) was extracted by fixing the depth of z at the tube location. The image of FIG. 9B was formed in this manner.

FIG. 9A illustrates a USF image of the tube on the x-y plane. The two vertical dashed lines indicate the locations of the inner edges of the tube. The FWHM and the full-width-at-one-eighth-of-the-maximum (FWEM) of the USF image profile along the x direction at each y location were calculated. The averaged FWHM and FWEM at different y locations were 0.48±0.13 mm and 0.68±0.19 mm, respectively. Although the FWHM (0.48 mm) is narrower than the inner diameter of the tube, the FWEM (0.69 mm) is very close to the tube's inner diameter (0.69 mm). Because the inner diameter can be considered to be a parameter describing the full size of the tube, the FWEM rather than the FWHM can be considered to be a parameter describing the full size of the USF image.

To compare the USF image with a pure ultrasound image, the same sample was scanned on the x-y plane using the same HIFU transducer via the commonly used pulse-and-echo method. At each x-y location, the reflected ultrasonic echo from the top inner boundary of the tube was recorded and used to generate the ultrasound image. The result is shown in FIG. 9B. Its averaged FWHM and FWEM were 0.76±0.01 mm and 1.12±0.02 mm, respectively. Both of these values are larger than those of the USF image. Moreover, if one assumes that the ultrasound speed in muscle is between 1,542 and 1,626 m/s, then the theoretical diffraction-limited lateral focal size (equivalent to the FWHM) of the adopted HIFU transducer (frequency=2.5 MHz and f-number=0.83) is between 0.512 and 0.54 mm, which is also larger than the average FWHM of the USF profiles of the tube. Therefore, methods of imaging described herein can achieve a resolution beyond the acoustic diffraction limit.

FIGS. 9C and 9D illustrate comparisons of the intensity profiles of USF-generated fluorescence, diffused fluorescence light, ultrasound, and temperature along the horizontal dashed line marked in FIG. 9A. In particular, FIG. 9C illustrates the profiles of the USF signal and the diffused fluorescence signal along the x axis at y=0. FIG. 9D illustrates the profiles of the USF, ultrasound, and temperature signals along the x axis at y=0. Both the USF and ultrasound images were normalized and interpolated based on a bicubic method. The FWHM of the diffused fluorescence signal was 3.9 mm, which is significantly larger than the FWHM of the corresponding USF image's profile (0.48 mm) and the tube's inner diameter (0.69 mm). Thus, methods described herein can provide improved resolution compared to diffused fluorescence methods such as fluorescence diffuse optical tomography (FDOT). It should also be noted that the temperature profile had a FWHM of 0.66 mm and the ultrasound profile had a FWHM of 0.76 mm in FIG. 9D, compared to a USF signal profile FWHM of 0.54 mm. To acquire the profile of the diffused fluorescence light, as illustrated in FIG. 9C, the sample was scanned along the x direction while all the other components remained fixed. Although the HIFU remained off and the temperature was kept at room temperature (<LCST), the USF contrast agents still emitted some fluorescence when the laser was on because the USF contrast agents are not 100 percent off even in the off state. To avoid distortion of the results by emission filter leakage of the excitation light, a background scan was conducted by filling the tube with water, and this background data was subtracted from the result acquired from the tube containing the fluorophores.

Example 3

Ultrasound-Switchable Fluorophores

General

A series of ultrasound-switchable fluorophores suitable for use in some embodiments of methods described herein were prepared as follows. The fluorophores comprised a plurality of FRET donor species and a plurality of FRET acceptor species either (1) coupled to a linear thermoresponsive polymer structure, (2) dispersed within a thermoresponsive polymer NP such as the NPs described hereinabove in Example 1, (3) coupled to the surface of a thermoresponsive polymer NP, or (4) partially dispersed within and partially coupled to the surface of a thermoresponsive polymer NP. Structures (1), (3), and (4) are illustrated schematically in FIGS. 10-12, respectively. In addition, some properties of various fluorophores are provided in Tables 2 and 3. Table 2 describes properties of fluorophores based on linear thermoresponsive polymer structures. Table 3 describes properties of fluorophores based on thermoresponsive polymer nanoparticles. The nomenclature used in Tables 2 and 3 corresponds to the nomenclature described further hereinbelow in this Example. In addition, measured values reported in Tables 2 and 3 were obtained in the manner described in Examples 1 and 2 above.

Structure (1)

In general, thermoresponsive linear polymers were first synthesized and then fluorescent species were grafted onto the polymer by forming covalent chemical bonds between appropriate moieties on the polymer and the fluorescent species, such as hydroxyl, carboxyl, and/or amine moieties. In some cases, for instance, a carbodiimide coupling scheme was used. Conjugation could also be carried out in other ways. In general, the donor species had short excitation/emission wavelengths in the visible region, while the acceptor species had a red/NIR emission (long wavelength). A short wavelength excitation light (for the donor) was used to excite the system, so that little or no acceptor was excited to a fluorescent state. When a thermoresponsive polymer took on a globular conformation as described hereinabove, the distance between donors and/or acceptors decreased, leading to FRET from the donors to the acceptors. Therefore, the emission of the acceptor (in long wavelength) could be observed.

To form a series of fluorophores having the general Structure (1), the following materials were used. N-isopropylacrylamide (NIPAM), N-tert-butylacrylamide (TBAm), acrylamide (AAm), acrylic acid (AAc), allylamine (AH), N,N,N',N'-tetramethyl ethylene diamine (TEMED), ammonium persulfate (APS), N-(3-Dimethylaminopropyl)-N'-ethylcarbodiimide hydrochloride (EDC), sodium dodecyl sulfate (SDS), N,N'-methylenebisacrylamide (BIS), and 7-(2-Aminoethylamino)-N,N-dimethyl-4-benzofurazansulfonamide (DBD-ED) were purchased from Sigma-Aldrich (St. Louis, Mo., USA). SeTau 425 mono-N-hydroxysuccinimide (NHS), Square 660 mono-NHS, Seta 700 mono-NHS, Seta 633 mono-NHS and Square 660 mono-NH2 were purchased from SETA BioMedicals (Urbana, Ill., USA), and denoted as ST425, Sq660, St700, Sq633, and Sq660a, respectively. All chemicals were used as received without further purification.

The thermoresponsive polymer components of the fluorophores having the general Structure (1) included at least three functional portions: (a) a primary thermoresponsive unit (such as NIPAM); (b) a LCST-controlling unit (such as TBAm or AAm); and (c) a functionalization unit (such as AAc or AH) for coupling to a fluorescent species. Linear polymers were synthesized through free radical polymerization. All reactions were carried out in a 250 mL Schlenk tube. The three main steps were as follows. First, a purging procedure was carried out wherein the reaction mixture was purged with nitrogen for 10 minutes. When an initiator (e.g., APS) or accelerator (e.g., TEMED) was added, oxygen was purged by three cycles of applying vacuum (1 m) and back-filling with nitrogen (5 s). Next, the polymerization reaction was carried out by stirring the reaction mixture under nitrogen for 4 h at room temperature. Finally, the polymer products were purified by dialysis with an appropriate molecular weight cut-off (MWCO) membrane for three days to remove unreacted monomers, initiator, and other small molecules.

Using P(NIPAM-AAc 200:1) as one example, a general procedure is as follows. Samples of 1.3644 g NIPAM (monomer) and 4 µL AAc (monomer) at a molar ratio of 200:1 were dissolved in 50 mL deionized (DI) water in the Schlenk tube. During the purging procedure, 0.067 g APS (initiator) and 51 µL TEMED (accelerator) were added into the tube. After the reaction, the sample was dialyzed with a 3.5K MWCO membrane. The resulting solution was collected and freeze-dried for subsequent conjugation with amine-containing fluorescent species. For the conjugation with NHS-containing fluorescent species, the amine-functionalized polymer P(NIPAM-AH) was synthesized using the same protocol as above, except using AH instead of AAc. More generally, the foregoing procedure was used to synthesize the following thermoresponsive polymers: P(NIPAM-TBAm-AAc 85:15:1), P(NIPAM-TBAm-AAc 185:15:1), P(NIPAM-TBAm-AAc 585:15:1), and P(NIPAM-AAm-AAc 200:32:1).

After the synthesis of the polymers, conjugation between the polymers and fluorescent species was carried out using chemical reactions between carboxyl and primary amine moieties. In some cases, the fluorescent species included NHS, which was reacted with a primary amine of the thermoresponsive polymer (such as an amine present in P(NIPAM-AH)). In other cases, the fluorescent species included a primary amine that was conjugated with a carboxyl group of the polymer (such as P(NIPAM-AAc)) in the presence of EDC. The conjugation reaction was carried out in a 7 mL brown glass tube to protect light-sensitive dyes or fluorescent species. The general procedures for conjugation were as follows. For amine-containing dyes (such as DBD-ED or Sq660a), 5 mg polymer, 25 mg EDC, and 0.3 mg DBD-ED or/and 5 µL Sq660a (stock solution of 1 mg/100 µL dimethyl sulfoxide (DMSO)) were dissolved in 5 mL deionized water in the tube. Then the tube was stirred and reacted overnight at room temperature. After completion of the reaction, the conjugates were purified with appropriate MWCO dialysis membranes as described above. For NHS-containing dyes (such as ST425, St633, Sq660, and St700), 5 mg polymer and 10 µL dye (stock solution: 1 mg/100 µL DMSO) were dissolved in 5 mL phosphate buffered saline (PBS, 8 mM sodium phosphate, 2 mM potassium phosphate, 0.14 M NaCl, 10 mM KCl, pH 8.3-8.6). Then the solution was stirred and reacted overnight at room temperature. Next, 1 mL of 20 mM Tris buffer (pH 7.8) was added to the solution to quench the unreacted NHS moieties of the dye for two hours. Finally, the sample was purified by dialysis.

It should be noted that, in some cases, DBD-ED, St633, Sq660, and St700 were used as polarity-sensitive fluorophores. In other instances, DBD-ED or ST425 was used as a donor species and Sq660(a) was used as an acceptor.

Structure (2)

Fluorophores having the Structure (2) were prepared as described above in Example 1.

Structure (3)

Fluorophores having the Structure (3) were prepared by first preparing thermoresponsive NPs as described in Example 1 above, except without including a fluorescent species. Next, fluorescent species were attached to the surface of the NPs in a manner corresponding to that described above for linear thermoresponsive polymers, except 5 mL polymer NP solution was used rather than 5 mg linear polymer. As one example fluorophore having the Structure (3), P(NIPAM-AAc 200:1) NPs-DBD-ED-Sq660a was prepared by covalently bonding two amine-containing dyes (DBD-ED and Sq660a) to the surface of the polymer NPs (P(NIPAM-AAc 200:1) NPs) through carboxyl moieties provided by the AAc monomer.

Structure (4)

Fluorophores having the Structure (4) were prepared by first preparing thermoresponsive NPs as described in Example 1 above and then conjugating fluorescent species to the surface of the NPs as described above for Structure (3). As one example fluorophore having the Structure (4), DBD-ED was encapsulated inside P(NIPAM-AH 86:14) NPs and Sq660 was attached to the surface of the NPS via conjugation of NHS moieties (from the dye) and amine moieties (from the AH monomer). Such fluorophores are denoted using the general nomenclature DBD-ED@P(NIPAM-AH 86:14) NPs-Sq660, where the species preceding the symbol "@" is encapsulated in the identified polymer NPs, and the species following the hyphen "-" is conjugated to the surface of the NPs.

TABLE 2

|  | Fluorophore | $\lambda_{ex}$ & $\lambda_{em}$ (nm) | $I_{On}/I_{Off}$ | $\tau_{On}/\tau_{Off}$ & $\tau_{On}$ (ns) | $T_{th}$ (° C.) | $T_{BW}$ (° C.) |
|---|---|---|---|---|---|---|
| DBD (Donor) | PNIPAM (chain), co-polymerization | 470 & 580 | 4.2 | 3.5 & 14 | 31 | 1 |
|  | P(NIPAM-AAc 100:1), post-labeling | 470 & 560 lp | 1.4 | 4.7 & 4.8 | 35 | 8 |
|  | P(NIPAM-AAc 200:1), post-labeling | 470 & 560 lp | 1.6 | 3.1 & 5.2 | 36 | 5 |
|  | P(NIPAM-AAc 600:1), post-labeling | 470 & 560 lp | 1.6 | 1.9 & 2.5 | 32 | 5 |
|  | P(NIPAM-TBAm-AAc 185:15:1), post-labeling | 470 & 560 lp | 1.8 | 5.4 & 10 | 26 | 4 |
|  | P(NIPAM-AAm-AAc 200:32:1), post-labeling | 470 & 560 lp | 1.1 | 2 & 2.2 | 42 | 9 |
| Red dyes (acceptor) | P(NIPAM-AH 200:1), post-labeling, St633 | 609 & 650/60 | 4.2 | 1.1 & 0.9 | 32 | 5 |
|  | P(NIPAM-AH 200:1), post-labeling, Sq660 | 609 & 711/25 | 1.6 | 2.2 & 2.1 | 35 | 3 |
|  | P(NIPAM-AH 200:1), post-labeling, St700 | 609 & 711/25 | 0.6 | 0.7 & 1.1 | 33 | 8 |
| FRET | P(NIPAM-AAc 200:1)-DBD-ED, -Sq660a, post-labeling | 470 & 711/25 | 3.8 | 3.4 & 5.3 | 34 | 3 |
|  | P(NIPAM-TBAm-AAc 185:15:1), -DBD-ED, -Sq660a, post-labeling | 470 & 711/25 | 3 | 1.7 & 5.3 | 26 | 3 |

TABLE 3

|  | Fluorophore | $\lambda_{ex}$ & $\lambda_{em}$ (nm) | $I_{On}/I_{Off}$ | $\tau_{On}/\tau_{Off}$ & $\tau_{On}$ (ns) | $T_{th}$ (° C.) | $T_{BW}$ (° C.) |
|---|---|---|---|---|---|---|
| DBD (donor) | @PNIPAMNPs, encapsulated | 470 & 560 lp | 4 | 3.3 & 6 | 35 | 5 |
|  | @P(NIPAM-AAm 86:14) NPs, encapsulated | 470 & 560 lp | 3.5 | 2.2 & 3.8 | 42 | 9 |

TABLE 3-continued

| | Fluorophore | $\lambda_{ex}$ & $\lambda_{em}$ (nm) | $I_{On}/I_{Off}$ | $\tau_{On}/\tau_{Off}$ & $\tau_{On}$ (ns) | $T_{th}$ (° C.) | $T_{BW}$ (° C.) |
|---|---|---|---|---|---|---|
| | @P(NIPAM-TBAm 185:15) NPs, encapsulated | 470 & 560 lp | 3.7 | 3.6 & 7.2 | 31 | 5 |
| | @P(NIPAM-AH 86:14) NPs, encapsulated | 470 & 560 lp | 3 | 2.6 & 5.3 | 33 | 8 |
| Red dyes (acceptor) | @PNIPAM NPs, encapsulated, St700 | 630 & 711/25 | 0.7 | 0.7 & 1.2 | 36 | 9 |
| | @PNIPAM NPs, encapsulated, Sq660 | 609 & 711/25 | 3.3 | 1.3 & 2.9 | 35 | 5 |
| FRET | DBD-ED@ P(NIPAM-AH 86:14) NPs-Sq660 | 470 & 711/25 | 6.9 | 1.4 & 3.42 | 35 | 7 |
| | P(NIPAM-AAc 200:1) NPs-DBD-ED-Sq660a | 470 & 711/25 | 5.3 | 3.3 & 6 | 35 | 5 |
| | P(NIPAM-TBAm-AAc 185:15:1) NPs-DBD-ED-Sq660a | 470 & 711/25 | 6.5 | 2.7 & 5.2 | 33 | 9 |
| | P(NIPAM-AAc 200:1) NPs-ST425-Sq660a | 456 & 711/25 | 7 | 1.5 & 3.65 | 36 | 4 |

Example 4

Ultrasound-Switchable Fluorophores

General

Figure 13:
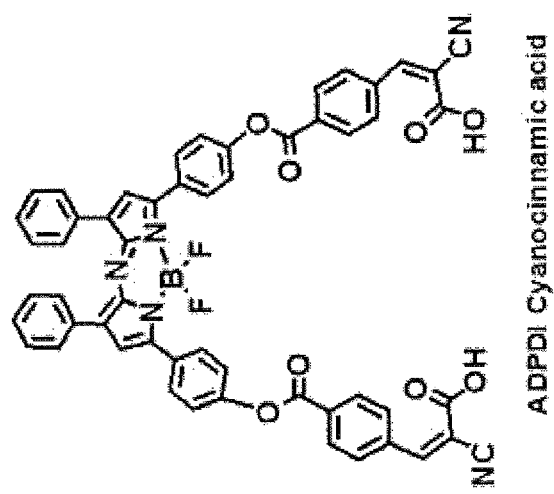
FIG. 13 illustrates the structure of a component of a fluorophore suitable for use in some embodiments of methods described herein.

A series of ultrasound-switchable fluorophores suitable for use in some embodiments of methods described herein were prepared as follows. The fluorophores comprised a thermoresponsive polymer and a fluorescent material with an emission peak in the red/NIR portion of the electromagnetic spectrum. In particular, ADPDI cyanocinnamic acid dye (ADPDICA) was used. The structure of ADPDICA is illustrated in FIG. 13. Some fluorophores were of the general Structure (1) from Example 3 hereinabove; other fluorophores were of the general Structure (2) from Example 3; and still other fluorophores were of the general Structure (3) from Example 3.

Materials

N-isopropylacrylamide (NIPAM), acrylamide (AAm), ammonium persulfate (APS), sodium dodecyl sulfate (SDS), N,N,N',N'-tetramethyl ethylene diamine (TEMED), N,N'-methylenebisacrylamide (BIS), acrylic acid (AAc), N-tert-butylacrylamide (TBAm), and sodium ascorbate were purchased from Sigma-Aldrich (St. Louis, Mo., USA). All chemicals are used as received without further purification.

Synthesis

ADPDICA was prepared according to the azadipyrromethene synthesis procedures described in Bandi et al., "Excitation-Wavelength-Dependent, Ultrafast Photoinduced Electron Transfer in Bisferrocene/BF$_2$—Chelated-Azadipyrromethene/Fullerene Tetrads," Chem. Eur. J. 2013, 19, 7221-7230, and Bandi et al., "Self-Assembled via Metal-Ligand Coordination AzaBODIPY-Zinc Phthalocyanine and AzaBODIPY-Zinc Naphthalocyanine Conjugates: Synthesis, Structure, and Photoinduced Electron Transfer," J. Phys. Chem. C 2013, 117, 5638-5649. Briefly, 3-(4-hydroxyphenyl)-1-phenylprop-2-en-1-one was first prepared by reacting the corresponding 4-hydroxybenzaldehyde, acetophenone, and potassium hydroxide. This species was subsequently reacted with nitromethane and diethylamine in dry ethanol to obtain 3-(4-hydroxyphenyl)-4-nitro-1-phenylbutan-1-one. Next, 4-{2-[3-(4-hydroxyphenyl)-5-phenyl-1H-pyrrolylimino]-5-phenyl-2H-pyrrol-3-yl}phenol was synthesized by reaction with ammonium acetate in ethanol. Then, BF$_2$-chelated 4-{2-[3-(4-hydroxyphenyl)-5-phenyl-1H-pyrrol-2ylimino]-5-phenyl-2H-pyrrol-3-yl}phenol was formed from this product by treating the product with diisopropylethylamine and boron trifluoride diethyl etherate in dry CH$_2$Cl$_2$. The BF$_2$-chelated species was then reacted with the appropriate benzoic acid in the presence of 1-ethyl-3-(3-dimethylaminopropyl)carbodiimide (EDCI) followed by chromatographic purification.

Fluorophores having the general Structure (1) were prepared according to the protocol described for Structure (1) in Example 3 above, except ADPDICA was used as the fluorescent species. In addition, purification was carried out by dialysis for 3 days using a 3.5 kDa MWCO membrane. Thermoresponsive polymers included P(NIPAM-AH 200:1), P(NIPAM-TBAm-AH 185:15:1), and P(NIPAM-AAm-AH 172:28:1). Therefore, the following fluorophores of general Structure (1) were formed: (a) P(NIPAM-AH 200:1)-ADPDICA, (b) P(NIPAM-TBAm-AH 185:15:1)-ADPDICA, and (c) P(NIPAM-AAm-AH 172:28:1)-ADPDICA. The conjugation of ADPDICA to the thermoresponsive polymers was carried out by forming an amide bond between the carboxyl groups of ADPDICA and the amine groups provided by the AH repeating units of the polymer.

Fluorophores having the general Structure (2) were prepared according to the protocol described for Structure (2) in Example 3 above. In particular, the protocol corresponded to that for the DBD-Sq660 FRET system. One exemplary fluorophore formed in this manner was ADPDICA@P(NIPAM-AH 200:1) NPs, in which ADPDICA was encapsulated inside the NPs.

Fluorophores having the general Structure (3) were prepared according to the protocol described for Structure (3) in Example 3 above. In particular, the protocol corresponded to that for the DBD-Sq660 FRET system. One exemplary fluorophore formed in this manner was P(NIPAM-AH 200:1) NPs-ADPDICA, in which ADPDICA was attached to the surface of the NPs. As with Structure (1), the conjugation of ADPDICA to the thermoresponsive polymer was carried out by forming an amide bond between the carboxyl groups of ADPDICA and the amine groups provided by the AH repeating units of the polymer.

Fluorescence Imaging

The temperature-dependent fluorescence properties of the fluorophores described above were evaluated at two different excitation wavelengths ($\lambda_{ex}$=609 nm or 655 nm) and using a 711 nm/25 nm band pass emission filter. The temperature of the fluorophores was controlled by disposing the fluorophores in a temperature-controlled water bath. The results are provided in Tables 4 and 5. Table 4 provides data for $\lambda_{ex}$=609 nm. Table 5 provides data for $\lambda_{ex}$=655 nm. The data in Tables 4 and 5 labeled as "$\lambda_{ex}$" refers to the emission filters used, where "lp" refers to a long pass filter.

TABLE 4

| Fluorophore | $\lambda_{ex}$, $\lambda_{em}$ (nm) | $I_{On}/I_{Off}$ | $T_{th}$ (° C.) | $T_{BW}$ (° C.) |
|---|---|---|---|---|
| P(NIPAM-AH 200:1)-ADPDICA | 609, 711/25 | 75.45 | 33 | 7 |
| P(NIPAM-TBAm-AH 185:15:1)-ADPDICA | 609, 711/25 | 93.59 | 30 | 7 |
| P(NIPAM-AAm-AH 172:28:1)-ADPDICA | 609, 711/25 | 188.94 | 42 | 7 |
| ADPDICA @ P (NIPAM-AH 200:1) NPs | 609, 711/25 | 2.14 | 35 | 2 |
| P (NIPAM-AH 200:1)-NPs-ADPDICA | 609, 711/25 | 20.12 | 34 | 6 |

TABLE 5

| Fluorophore | $\lambda_{ex}$, $\lambda_{em}$ (nm) | $I_{On}/I_{Off}$ | $T_{th}$ (° C.) | $T_{BW}$ (° C.) |
|---|---|---|---|---|
| P(NIPAM-AH 200:1)-ADPDICA | 655, 711/25 | 319.95 | 33 | 7 |
| P(NIPAM-TBAm-AH 185:15:1)-ADPDICA | 655, 711/25 | 417.2 | 30 | 7 |
| P(NIPAM-AAm-AH 172:28:1)-ADPDICA | 655, 711/25 | 274.46 | 42 | 7 |
| ADPDICA@P(NIPAM-AH 200:1) NPs | 655, 711/25 | 1.79 | 35 | 2 |
| P(NIPAM-AH 200:1)-NPs ADPDICA | 655, 711/25 | 43.38 | 34 | 6 |

Example 5

Methods of Imaging Using Microbubbles

Methods of imaging according to some embodiments described herein were carried out as follows. First, a series of fluorophores comprising microbubbles was prepared. In one case, the fluorophores included Targestar-B microbubbles having a plurality of FRET acceptor species (or "fluorophore" species, abbreviated as "F") and a plurality of FRET donor species (or "quencher" species, abbreviated as "Q") attached to the exterior surface of the microbubbles. Specifically, Alexa Fluor (AF) 546 (donor or F) and AF 647 (acceptor or Q) were labeled on the microbubble surface via biotin-streptavidin coupling.

For imaging, the intensity of the excitation light (532 nm) was modulated at 15 MHz. Individual F-Q microbubbles were flowed slowly through an ultrasonically and optically transparent microtube. An ultrasound burst with three cycles at a central frequency of 2.25 MHz was used to expand the F-Q microbubbles. Initially, the fluorescence signal from the AF 546 was weak due to FRET energy transfer from AF 546 to AF 647. However, the fluorescence emission from AF 546 could be ultrasonically switched on (with an $I_{On}/I_{Off}$ ratio of about 5 and a $\tau_{On}/\tau_{Off}$ ratio of about 5) due to the expansion of the microbubbles during the negative pressure cycles formed by the ultrasound bursts. The emission from the acceptor (AF 647) displayed a complementary behavior.

It was discovered that a well-confined ultrasonic negative pressure field could be formed using two diffraction-limited ultrasound beams for F-Q-microbubble-based USF imaging. The ultrasound beams were provided by two focused 5 MHz transducers. The FWHM of the lateral size of the focused negative pressure region of each beam was about 450 µm. This size was determined primarily by the diffraction and numerical aperture (NA) of the transducer. The axial size of the focus was about 380 µm. This size was primarily determined by the ultrasound pulse length and frequency and the transducer (assuming the axial resolution is at least half of the pulse width multiplied the ultrasound speed). When the two ultrasound pulses perpendicularly propagated and crossed each other at the common focal zones, an interfered pressure field was obtained by summing the two individual, perpendicular fields. In this manner, a small negative pressure region was formed, wherein the small region had a size smaller than the focal zone of either beam used to form the region. The FWHM of the main negative pressure region (MNPR) formed by the two beams was about 165 µm in the lateral direction, which was about 2.7 times and 2.3 times narrower than the lateral and axial resolutions of the individual ultrasound pulses, respectively. A similar result was found in the axial direction of the interfered field.

While the MNPR was spatially confined, it was also temporally limited due to the propagation of the ultrasound pulses. The lifetime of the confined MNPR was approximately 0.08-24 µs. This time period was long enough to permit illumination of surrounding tissue using ps light pulses to excite the fluorophores in the on state. It was also much longer than the width of the excitation light pulses, which may be widened to 1-3 ns in deep tissue due to light scattering in the tissue. Therefore, if needed, multiple light pulses could be provided in a single time window. By optically illuminating the tissue only within this time window (i.e., temporally confining the excitation), it was possible to avoid background fluorescence noise generated by fluorophores unexpectedly switched-on by the individual ultrasound pulses before and after the formation of the MNPR. Thus, the USF fluorescence signal could be detected only when both optical and ultrasonic pulses were spatially and temporally overlapped.

Figure 14:
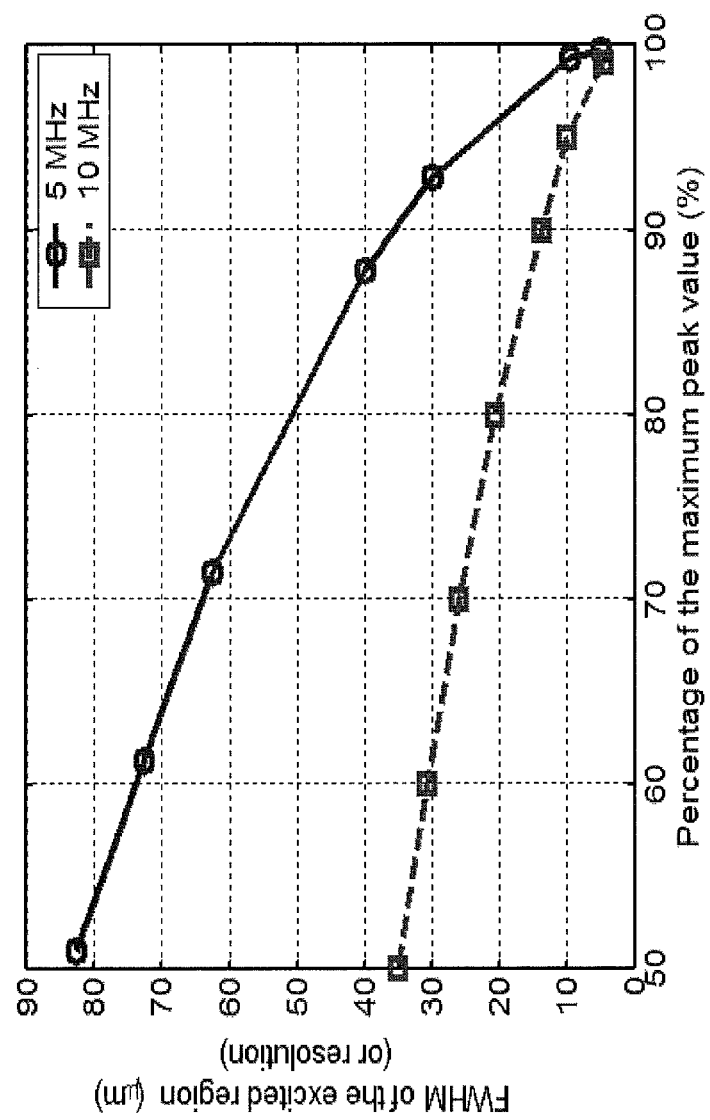
FIG. 14 illustrates a plot of imaging resolution versus fluorophore switching threshold for some embodiments of methods described herein.

In addition, it was discovered that the spatial resolution of imaging methods described herein, in some embodiments, could be further improved by appropriately selecting the pressure threshold to oscillate a microbubble described herein. For example, assuming a negative pressure threshold of 100 kPa and a negative peak pressure in each individual ultrasound pulse below this threshold, the fluorophores would not be switched on until the two ultrasonic pulses are overlapped and the MNPR is formed. When two ultrasonic pulses described above are used to form the MNPR, the maximum negative pressure of the interference field is doubled (200 kPa) due to constructive interference. Only the F-Q microbubbles within the region where the pressure is above 100 kPa can be switched on. The full size of this region is about 165 μm and its FWHM (the spatial resolution) is about 83 μm. However, even smaller activation region sizes and even high resolution powers can be obtained by further adjusting the relationship between the switching threshold value (e.g., 100 kPa) and the peak negative pressure provided by each individual ultrasonic beam. When the negative pressure switching threshold increases (becomes more negative), the size of the region in which F-Q microbubbles can be switched on decreases, and therefore the spatial resolution is improved. FIG. 14 illustrates the relationship between the FWHM of the activation region in which F-Q microbubbles are switched on and the threshold value of the microbubbles, wherein the switching threshold is represented as a percentage of the maximum negative pressure of an individual ultrasound beam. When the threshold is above about 70 percent of the maximum negative pressure, the resolution is quickly improved for both 5 and 10 MHz ultrasound frequencies. For example, when the threshold is 90 percent of the maximum negative pressure, the spatial resolution can reach 14 μm and 35 μm for the 10 MHz and 5 MHz ultrasound frequencies, respectively, which is significantly improved compared to the pure ultrasonic lateral and axial resolutions (450 μm and 380 μm).

In general, improvement of spatial resolution can be accompanied by the degradation of signal-to-noise ratio (SNR). This degradation can be due to the smaller volume of the activation region. At a given concentration of fluorophores, fewer fluorophores may be likely to be found in a smaller volume of a biological environment. As a result, fewer fluorophores may be available in an on state to be excited and a weaker USF signal may be expected. The extreme, non-zero case occurs when only a single F-Q microbubble is located in an image voxel (such as 30 μm×30 μm×30 μm voxel). Typically, a 2-μm-diameter microbubble can be labeled with $5\times10^4$ molecules/μm$^2$, based on the volume of the microbubble, which is equivalent to a volume concentration of 249 μM, using the bubble's volume to calculate the concentration. If the volume is taken to be a 30 μm×30 μm×30 μm voxel, then this labeling amount is equivalent to a volume concentration of 36 nM. These concentrations are far above the detection limits (fM-nM) of most optical techniques for tissue imaging. Therefore, using a highly sensitive optical detection system (such as a time-gated and/or photon counting system) can substantially compensate for any loss in SNR due to the small activation region volume, and it is possible to detect a single F-Q microbubble in tissue.

Example 6

Ultrasound-Switchable Fluorophores

Additional ultrasound-switchable fluorophores suitable for use in methods according to some embodiments described herein include the following.

F-Q-HJ Microbubbles

Figure 15:
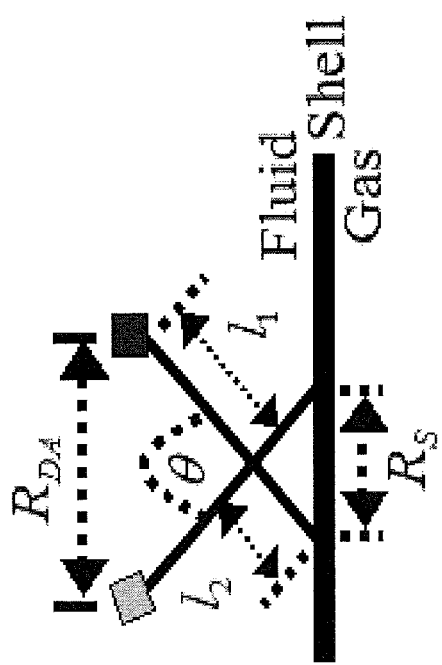
FIG. 15 illustrates an ultrasound-switchable fluorescence process according to one embodiment of a method described herein.

To implement FRET between a donor-acceptor pair on a microbubble's surface, a donor and an acceptor can be labeled on a microbubble via a Holliday junction (HJ). FIG. 15 illustrates such a microbubble schematically. The two crossed lines represent two arms of the HJ, which is composed of four DNA double helices in the form of a four-way junction. The two squares indicate a pair of donor and acceptor species that are labeled at the two ends of the two arms (via streptavidin-biotin coupling or through the reaction between the nucleic acids of the HJ and an NHS ester attached to the donor and acceptor). The horizontally oriented line indicates the shell of the microbubble on which the other two ends of the HJ are attached (via biotin-streptavidin coupling or another coupling scheme). When the bubble is expanded (compressed), the distance $R_S$ is increased (decreased). This results in the increase (decrease) of the distance between the donor and the acceptor ($R_{DA}$) with a magnification of ($I_1/I_2$) and concomitant switching on (off) of the donor. The initial angle (0) between the two arms can be controlled. Due to the relatively large surface area of a microbubble, numerous F-Q-HJs may be labeled on a single microbubble without significant interference. Such a design can narrow the USF transition band and improve ultrasound-switching efficiency and SNR.

F-Q-Hairpin-NP Microbubbles

Figure 16:
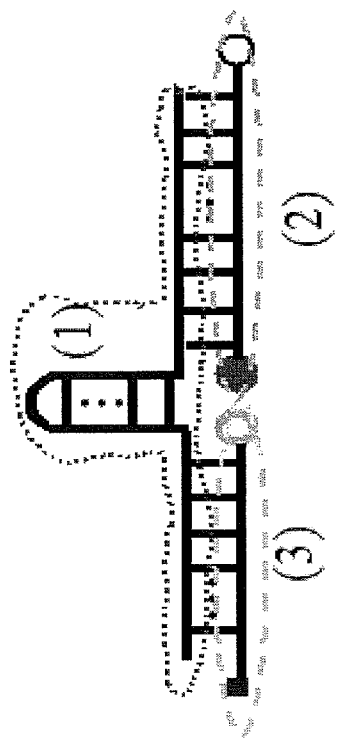
FIG. 16 illustrates an ultrasound-switchable fluorescence process according to one embodiment of a method described herein.
Figure 17:
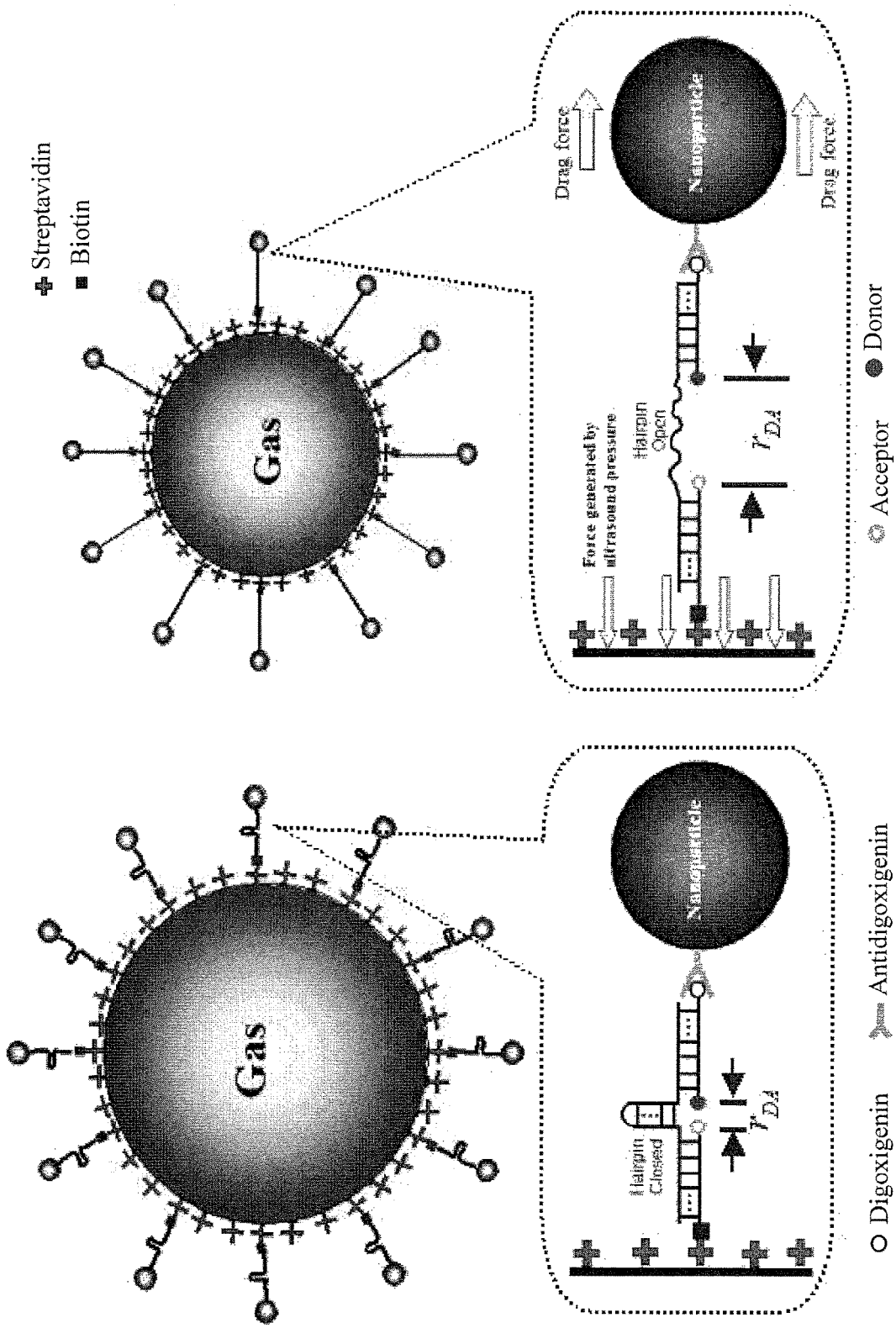
FIG. 17 illustrates an ultrasound-switchable fluorescence process according to one embodiment of a method described herein.

Another labeling strategy is to attach a donor-acceptor pair on a DNA hairpin complex (see FIGS. 16 and 17). One end of the hairpin complex is attached to a microbubble surface via biotin-streptavidin coupling, and the other end is attached to a much smaller gold nanoparticle (Au—NP, tens of nm in diameter) via digoxigenin-antidigoxigenin coupling. The F-Q (or D-A) labeled DNA hairpin complex consists of three major components: (1) a hairpin molecule (dotted region in FIG. 16), (2) an oligonucleotide attached to a donor and a digoxigenin, and (3) an oligonucleotide attached to an acceptor and a biotin. Not intending to be bound by theory, the principle to switch on the donor can be described as follows. An ultrasound pressure wave can accelerate the microbubble wall and therefore accelerate the Au nanoparticle by stretching the hairpin molecule. The accelerated Au—NP applies an opposite force on the hairpin molecule. When this force is large enough, the hairpin loop can be opened, thereby increasing the donor-acceptor distance and switching on the donor. A force of about 18 picoNewton (pN) can be used to open a hairpin and turn on the donor emission. When the force is reduced to less than about 6 pN, the hairpin is closed and the donor is switched off. It is estimated that an ultrasound pulse with a 150 kPa pressure wave applied to a microbubble with a diameter of 2 μm and attached to an Au—NP with a diameter of 20 nm can generate a force of about 20 pN to stretch the hairpin molecules. Therefore, it is possible to ultrasonically switch on the fluorescence.

F-Q-Hairpin Microbubbles

It is also possible to replace the Holliday Junction of the F-Q-HJ microbubbles above with a DNA hairpin molecule described above. Its two ends can be annealed to two complementary oligonucleotides. One oligonucleotide is labeled with a donor (such as AF 610) and a biotin. Similarly, the other oligonucleotide is attached to an acceptor (such as AF 647) and a biotin. The biotin ends can be attached to a streptavidin-labeled microbubble. When the length of the DNA molecule is shorter than its persistent length (usually about 50 nm), the DNA molecule behaves like an elastic rod. Therefore, the two arms are naturally stretched and attached to the microbubble surface. When exposure to an ultrasound beam expands the microbubble during a negative pressure cycle, a force is applied on the two ends of the hairpin arms, which can open the hairpin and switch on the donor as described above.

F-Q-DNA-NP Microbubbles

It is also possible to attach a microbubble with relatively small nanoparticles (tens of nm) via fluorescence-labeled double stranded (ds) DNA molecules. The ds-DNA is attached to the microbubble surface via biotin-streptavidin coupling. The other end of the ds-DNA is attached to a gold nanoparticle (Au NP) via a thiol linkage. Normally the ds-DNA is bent and flatly absorbed to the surface of the AuNP due to electrostatic attraction, hydrophobic interactions, and ion-dipole dispersive interactions between the ds-DNA and the AuNP. Due to the attraction between the Au NP and the DNA molecule, the Au NP is close to the fluorescent species that are labeled on one end of the ds-DNA. The surface of the AuNP can quench the fluorescent species within a relatively long distance (about 3-20 nm). When an ultrasound pressure wave is applied to compress the microbubble, the accelerated microbubble wall will accelerate the Au NP by stretching the ds-DNA molecule. When the acceleration of the microbubble wall is sufficiently large (controlled by ultrasound pressure strength) that the forces generated by the electrostatic attraction and other interactions between the DNA and the Au NP, the Au NP cannot experience the same acceleration (due to the mass of the AuNP), resulting in separation of the fluorescent species from the Au NP surface and removal of the quenching effect.

QD-Thermoresponsive Polymer-Acceptor Fluorophores

Another FRET-based fluorophore uses a semiconductor quantum dot such as a CdSe quantum dot as a donor and a small molecule dye as an acceptor. The quantum dot is attached to one or more acceptor dyes using one or more linkers formed from a thermoresponsive polymer. For example, a red-emitting quantum dot (Qdot® 655, Invitrogen, Inc.) is selected as a donor and a NIR dye (Alexa Fluor 750, Invitrogen, Inc.) as the acceptor. Multiple acceptors (AF 750) are attached on a single donor (Qdot® 655) via thermoresponsive polymers using coupling schemes described hereinabove. The QD donor has a very long lifetime (approximately 30 ns) and the acceptor AF 750 has a very short lifetime (approximately 0.7 ns). When T<LCST, the thermoresponsive polymer exhibits an extended coil or chain conformation, which is relatively long. Therefore, the distances between the donor and acceptors are generally longer than the FRET quenching range (>40 nm). When a HIFU transducer heats the thermoresponsive polymer above its LCST in a manner described hereinabove, the polymer makes a transition to a globular conformation, thereby reducing the donor-acceptor distances (<20 nm). As a result, FRET energy transfer occurs. Accordingly, part of the excitation energy of the donor (Qdot® 655) is transferred to the acceptors (AF 750), which emit photons at NIR wavelengths. These FRET-related photons can have a lifetime close to the longer of the donor lifetime and the acceptor lifetime, which is approximately 30 ns in this case. Thus, the emitted NIR photons can be readily detected with high SNR using a time-gated detection technique described herein. A long pass optical filter can be used to eliminate detection of the QD emission.

Various embodiments of the present invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. A method of imaging comprising:
   disposing a population of ultrasound-switchable fluorophores in a biological environment, the fluorophores having a switching threshold temperature ($T_{th}$) or a switching threshold pressure ($P_{th}$) between an off state and an on state;
   creating an activation region within the biological environment by exposing the biological environment to an ultrasound beam, the activation region having a maximum negative pressure ($P_{max}$) and a maximum temperature ($T_{max}$);
   switching at least one of the fluorophores within the activation region from the off state to the on state;
   exciting the at least one fluorophore with a beam of electromagnetic radiation; and
   detecting light emitted by the at least one fluorophore,
   wherein the switching threshold pressure ($P_{th}$) of the fluorophores is from 0.5 times to 1 times the maximum negative pressure ($P_{max}$) of the activation region, or the switching threshold temperature ($T_{th}$) of the fluorophores is from 0.5 times to 1 times the maximum temperature ($T_{max}$) of the activation region.

2. The method of claim 1, wherein:
   the fluorophores have a switching threshold temperature ($T_{th}$) between an off state and an on state; and
   the activation region has a maximum temperature ($T_{max}$); and
   $T_{th}$ is from 0.5 times to 1 times $T_{max}$.

3. The method of claim 1, wherein the biological environment is exposed to a plurality of ultrasound beams from a plurality of different directions, the focal zones of the ultrasound beams at least partially overlapping.

4. The method of claim 3, wherein $P_{th}$ is greater than the maximum negative pressure provided by the focal zone of one of the ultrasound beams alone, or $T_{th}$ is greater than the maximum temperature provided by the focal zone of one of the ultrasound beams alone.

5. The method of claim 1 further comprising exposing the biological environment to a pulsed beam of electromagnetic radiation prior to exposing the biological environment to the ultrasound beam, the pulsed beam having a pulse duration of no greater than 100 picoseconds, based on a full width at half maximum of an optical power of the pulsed beam over time.

6. The method of claim 1, wherein the biological environment comprises deep tissue.

7. The method of claim 1, wherein the biological environment comprises tumor vasculature.

8. The method of claim 1, wherein at least one fluorophore comprises a microbubble having one or more FRET donor species and one or more FRET acceptor species attached to a surface of the microbubble.

9. The method of claim 1, wherein at least one fluorophore comprises a thermoresponsive polymer.

10. The method of claim 9, wherein the polymer comprises a poly(N-isopropylacrylamide) or a copolymer of N-isopropylacrylamide with one or more of acrylamide, N-tert-butylacrylamide, acrylic acid, and allylamine.

11. The method of claim 1, wherein the activation region has a smaller volume than a focal zone of the ultrasound beam.

12. The method of claim 1, wherein the method exhibits a penetration depth/resolution ratio of at least 100.

13. A method of imaging comprising:
  disposing a population of ultrasound-switchable fluorophores in a biological environment, the fluorophores having a switching threshold between an off state and an on state;
  exposing the biological environment to a pulsed beam of electromagnetic radiation, the pulsed beam having a pulse duration of no greater than 100 picoseconds, based on a full width at half maximum of an optical power of the pulsed beam over time;
  creating an activation region within the biological environment by exposing the biological environment to an ultrasound beam;
  switching at least one of the fluorophores within the activation region from the off state to the on state;
  exciting the at least one fluorophore with a second beam of electromagnetic radiation; and
  detecting light emitted by the at least one fluorophore.

14. The method of claim 13, wherein at least one fluorophore comprises a microbubble having one or more FRET donor species and one or more FRET acceptor species attached to a surface of the microbubble.

15. The method of claim 13, wherein at least one fluorophore comprises a thermoresponsive polymer.

16. The method of claim 13, wherein the activation region has a smaller volume than a focal zone of the ultrasound beam.

17. The method of claim 13, wherein the method exhibits a penetration depth/resolution ratio of at least 100.

18. A method of imaging comprising:
  disposing a population of ultrasound-switchable fluorophores in a biological environment, the fluorophores having a switching threshold temperature ($T_{th}$) or a switching threshold pressure ($P_{th}$) between an off state and an on state;
  creating an activation region within the biological environment by exposing the biological environment to a plurality of ultrasound beams from a plurality of different directions, focal zones of the ultrasound beams at least partially overlapping;
  switching at least one of the fluorophores within the activation region from the off state to the on state;
  exciting the at least one fluorophore with a beam of electromagnetic radiation; and
  detecting light emitted by the at least one fluorophore, wherein the switching threshold pressure ($P_{th}$) of the fluorophores is greater than a maximum negative pressure ($P_{max}$) provided by a focal zone of one of the ultrasound beams alone, or the switching threshold temperature ($T_{th}$) of the fluorophores is greater than a maximum temperature ($T_{max}$) provided by a focal zone of one of the ultrasound beams alone.

19. The method of claim 18 further comprising exposing the biological environment to a pulsed beam of electromagnetic radiation prior to exposing the biological environment to the ultrasound beams, the pulsed beam having a pulse duration of no greater than 100 picoseconds, based on a full width at half maximum of an optical power of the pulsed beam over time.

* * * * *